US012778591B2

(12) United States Patent
Koo et al.

(10) Patent No.: US 12,778,591 B2
(45) Date of Patent: Nov. 3, 2026

(54) VASO-OCCLUSIVE DEVICES AND METHODS FOR MAKING AND USING SAME

(71) Applicants: STRYKER CORPORATION, Kalamazoo, MI (US); STRYKER EUROPEAN OPERATIONS LIMITED, Carrigtwohill (IE)

(72) Inventors: Esther Koo, Kalamazoo, MI (US); Clifford Teoh, Los Altos, CA (US); Stella Than Chu, Kalamazoo, MI (US); Jason Delgadillo, Kalamazoo, MI (US)

(73) Assignees: Stryker Corporation, Kalamazoo, MI (US); Stryker European Operations Limited, Carrigtwohill (IE)

( * ) Notice: Subject to any disclaimer, the term of this patent is extended or adjusted under 35 U.S.C. 154(b) by 77 days.

(21) Appl. No.: 18/667,790

(22) Filed: May 17, 2024

(65) Prior Publication Data

US 2024/0299035 A1 Sep. 12, 2024

Related U.S. Application Data

(63) Continuation of application No. PCT/US2022/078935, filed on Oct. 28, 2022.

(Continued)

(51) Int. Cl.

*A61B 17/12* (2006.01)
*A61B 17/00* (2006.01)

(52) U.S. Cl.

CPC .. *A61B 17/12113* (2013.01); *A61B 17/12145* (2013.01); *A61B 2017/00526* (2013.01); *A61B 2017/00867* (2013.01)

(58) Field of Classification Search

CPC .......... A61B 17/1214; A61B 17/12145; A61B 17/12113; A61B 17/12109; A61B 17/12118

See application file for complete search history.

(56) References Cited

U.S. PATENT DOCUMENTS

| | | | | |
|---|---|---|---|---|
| 4,994,069 A | 2/1991 | Ritchart et al. | | |
| 6,171,326 B1 * | 1/2001 | Ferrera | ............ | A61B 17/12113 606/191 |

(Continued)

FOREIGN PATENT DOCUMENTS

| | | |
|---|---|---|
| JP | 2001-525217 A | 12/2001 |
| JP | 2002-523172 A | 7/2002 |

OTHER PUBLICATIONS

PCT International Search Report and Written Opinion dated Feb. 8, 2024 for Int'l Application No. PCT/US2022/078935, (11 pages).

(Continued)

*Primary Examiner* — Kathleen S Holwerda

(74) *Attorney, Agent, or Firm* — Vista IP Law Group, LLP

(57) ABSTRACT

A vaso-occlusive device comprises a wire having a primary configuration in a constrained condition. The wire forms a secondary configuration in a relaxed, unconstrained condition. The secondary configuration comprises a pyramidal portion comprising a plurality of distal coils. Each distal coil is wound from the wire such that the winding has a perimeter which tapers outwardly from an interior of the pyramidal portion, and a transition segment of the wire between each distal coil and connecting each distal coil. The plurality of distal coils is arranged in a pyramidal shape such that each coil lies in a different lateral face of the pyramidal shape. The vaso-occlusive device may also include a body portion (Continued)

proximal of the pyramidal portion formed from the wire and extending proximally from the pyramidal portion.

7 Claims, 13 Drawing Sheets

Related U.S. Application Data

(60) Provisional application No. 63/281,561, filed on Nov. 19, 2021.

(56) References Cited

U.S. PATENT DOCUMENTS 6,322,576 B1 11/2001 Wallace et al.
6,616,617 B1 * 9/2003 Ferrera ............ A61B 17/12113 600/585
2008/0319532 A1 * 12/2008 Monstadt ......... A61B 17/12145 623/1.22
2019/0298387 A1 10/2019 Qin et al.
2021/0045749 A1 2/2021 Wang et al.
2023/0329720 A1 10/2023 Delgadillo et al.
2024/0016497 A1 1/2024 Eldridge et al.
2024/0299035 A1 9/2024 Koo et al.

OTHER PUBLICATIONS

Foreign OA for IN Patent Appln. No. 202447024993 dated Jan. 22, 2026.
Communication under Rule 71(3) EPC dated Oct. 18, 2024 for European Patent Application No. 22831035.5-1122, (8 pages).
Foreign OA for JP Patent Appln. No. 2024-529178 dated Jan. 20, 2026 (with English translation).

* cited by examiner

VASO-OCCLUSIVE DEVICES AND METHODS FOR MAKING AND USING SAME

RELATED APPLICATION DATA

This application is a continuation of International Patent Application No. PCT/US2022/078935, filed on Oct. 28, 2022, which claims priority to and the benefit of U.S. Provisional Patent Application No. 63/281,561, filed on Nov. 19, 2021. The entire disclosures of the above applications are expressly incorporated by reference herein.

FIELD OF THE INVENTION

The present disclosure relates generally to medical devices and intravascular medical procedures and, more particularly, to devices for occluding vascular defects, such as aneurysms and methods for making and using such devices.

BACKGROUND

Vaso-occlusive devices or implants are used for a wide variety of reasons, including treatment of intra-vascular aneurysms. An aneurysm is a dilation of a vessel, such as a blood vessel, that may pose a risk to a patient's health due to rupture, clotting, or dissection. For example, rupture of an aneurysm in a patient's brain may cause a stroke, and lead to brain damage and death. Cerebral aneurysms may be detected in a patient, e.g., following seizure or hemorrhage, and may be treated by applying vaso-occlusive devices.

Commonly used vaso-occlusive devices include soft, helically wound coils formed by winding a platinum (or platinum alloy) wire strand about a "primary" mandrel. The coil is then wrapped around a larger, "secondary" mandrel, and heat treated to impart a secondary shape. For example, U.S. Pat. No. 4,994,069, issued to Ritchart et al., which is fully incorporated herein by reference as though set forth in full, describes a vaso-occlusive device that assumes a linear, helical primary shape when stretched for placement through the lumen of a delivery catheter, and a folded, convoluted secondary shape when released from the delivery catheter and deposited in the vasculature. In order to better frame and fill aneurysms, complex three-dimensional secondary shapes can be imparted on vaso-occlusive devices and the stiffness/flexibility of vaso-occlusive devices can be modified.

In order to deliver the vaso-occlusive devices to a desired site in the vasculature, e.g., within an aneurysmal sac, it is known to first position a small profile delivery catheter or "micro-catheter" at the site using a guidewire. Typically, the distal end of the micro-catheter is provided, either by the attending physician or by the manufacturer, with a selected pre-shaped bend, e.g., 45°, 26°, "J", "S", or other bending shape, depending on the particular anatomy of the patient, so that it will stay in a desired position for releasing one or more vaso-occlusive device(s) into the aneurysmal sac once the guidewire is withdrawn. A delivery or "pusher" assembly or "wire" is then passed through the micro-catheter until a vaso-occlusive device coupled to a distal end of the delivery assembly is extended out of the distal end opening of the micro-catheter and into the aneurysmal sac. Once in the aneurysmal sac, portions of the vaso-occlusive device may deform or bend to allow more efficient and complete packing. The vaso-occlusive device is then released or "detached" from the distal end of the delivery assembly, and the delivery assembly is withdrawn back through the micro-catheter. Depending on the particular needs of the patient, one or more additional vaso-occlusive devices may be pushed through the micro-catheter and released into the same aneurysmal sac.

Fluoroscopy is typically used to visualize vaso-occlusive devices during delivery into an aneurysm, while magnetic resonance imaging (MRI) is typically used to visualize the treatment site post-procedure (e.g., a few weeks after initial treatment of the aneurysm) to ensure that the aneurysmal sac is properly occluded. As such, it is important that vaso-occlusive devices be constructed in a manner that enables their radiopacity during treatment of the aneurysm, while minimizing any visualization obscuring artifacts created during the post-procedure MRI (i.e., being MRI-compatible). It is also preferable that such vaso-occlusive devices be "soft" (i.e., be laterally flexible or conformable), and thus atraumatic, to prevent rupturing of the delicate tissues of the aneurysm.

It is also important that such vaso-occlusive devices be chronically retained within the aneurysm. However, aneurysms with larger mouths, commonly known as "wide neck aneurysms," present difficulty in the placement and retention of vaso-occlusive devices within the aneurysm sacs, particularly with small and relatively thin vaso-occlusive coils which lack sufficient mechanical strength to maintain their position within such aneurysm sacs no matter how skillfully they are placed. For instance, small aneurysms (e.g., aneurysm having diameters less than about 7 mm, or even smaller such as less than about 5 mm), often have the characteristics of a wide neck and a short dome. More specifically, small aneurysms often have relatively wide necks compared to the size of the aneurysm (i.e., the proportion of the width of the neck to the diameter of the aneurysm is often large for small aneurysms as compared to such proportion for larger aneurysms). Due to the relatively wide neck, small aneurysms (and wide neck aneurysms, in general) have greater risk of coil herniation into the parent vessel both during placement and retention. FIG. 1 depicts a portion of a vaso-occlusive coil herniating out of the aneurysm after implantation. To alleviate coil herniation during placement, several placement techniques have been developed. One such placement technique, called a "jailing technique," utilizes a balloon or stent deployed in the vessel adjacent to the neck region of the aneurysm to prevent the vaso-occlusive coils from exiting the aneurysmal sac. FIG. 2 depicts the jailing technique using a balloon activated catheter. The balloon activated catheter is used to deploy a balloon adjacent to the neck region of the aneurysm. The balloon prevents coils from herniating from the aneurysm as the latter are implanted into the aneurysm. However, as depicted in FIG. 2, this technique creates a risk of the balloon pushing the tip of the catheter into the dome of the aneurysm and rupturing the aneurysm. FIG. 3 depicts a jailing technique using a stent. The stent is placed and expanded around the neck of the aneurysm to block the coils from exiting the aneurysm sac. Similar to the balloon activated catheter, the stent technique also risks the stent pushing the tip of the catheter into the dome of the aneurysm and rupturing the aneurysm. FIG. 4 depicts another placement technique for implanting a vaso-occlusive device called "recrossing." In this technique, the delivery catheter extends through an opening in the stent. The stent prevents the coils from herniating out of the aneurysm sac. However, due to inherent unpredictability of positioning the delivery catheter through an opening of the stent, there is a risk that manipulation of the delivery catheter to direct and position the delivery catheter can cause the catheter tip to push into the dome thereby rupturing the aneurysm.

To address these herniation and implantation issues, vaso-occlusive coils have been developed which provide more neck coverage and shape stability to effectively "frame" an aneurysm. However, the three-dimensional shapes of current vaso-occlusive devices are either not conducive to framing or are prone to herniation during deployment into an aneurysm. Small aneurysms are best treated with as few coils as possible and current vaso-occlusive devices are not able to balance shape stability and softness as a standalone unit. Indeed, the shapes and configuration of current vaso-occlusive devices result in a directly proportional relationship between shape stability and softness. In other words, the softer the device (i.e., the less resistant to deformation from an external force), the less stable the device, and vice versa (i.e., the less soft the device, the more stable the shape of the vaso-occlusive device). Hence, a softer coil is less likely to rupture an aneurysm but is not able to retain its shape such that it is more prone to herniation out of the aneurysm during deployment and/or retention. Conversely, a stiffer coil is better able to retain its shape and frame the aneurysm, but imparts higher stresses on the aneurysm wall, creating high risk of rupturing the aneurysm, especially small aneurysms with a high rupture risk. In addition, particularly with outward complex shapes employed by current designs, the initial distal loops (e.g., first and second loops) have a higher likelihood of herniating out of the aneurysm due to subsequent loops pushing them out during deployment.

Accordingly, there is a need for vaso-occlusive devices which can alleviate the issues of herniation during placement and retention and provide effective framing of the aneurysm, and at the same time have a sufficiently soft and pliable structure that will not rupture the aneurysm, especially small, wide-necked aneurysms.

SUMMARY

In accordance with one aspect of the presently disclosed medical devices and intravascular medical procedures, a vaso-occlusive device comprises an elongate vaso-occlusive device (e.g., from 0.5 to 100 cm in length) configured for implantation in an aneurysm sac. The vaso-occlusive devices disclosed herein are not limited to being configured and used for treating small, wide-necked aneurysms, but they are particularly well-suited for such configuration and use. The vaso-occlusive device typically has a delivery configuration (having a primary shape) when restrained within a delivery catheter and a deployed configuration (having a secondary shape different from the primary shape) when released from the delivery catheter into the aneurysmal sac.

The vaso-occlusive device includes wire having a primary configuration in a constrained condition. For instance, the primary configuration may be a shape of the wire when it is constrained within a delivery catheter, such as a helical coil shape, linear shape, or the like. The wire is also configured to form into a secondary configuration in a relaxed, unconstrained condition, such as when the wire is released from a delivery catheter with no external forces exerting on the wire.

The secondary configuration of the wire provides a balanced solution between shape stability and softness such that the vaso-occlusive device has a stable shape which prevents herniation during deployment and retention and provides effective framing of the aneurysm, while also having sufficient softness/pliability to avoid rupturing the aneurysm. The pyramidal shape has an inherent ability to effectively dissipate forces applied to its apexes, thereby reducing the risk of imparting excessive forces on the walls of the aneurysm which could rupture the aneurysm. Accordingly, the secondary configuration includes a pyramidal portion comprising a plurality of distal coils wound from the wire. Each distal coil includes a winding forming a closed loop of greater than 360° wherein the winding has a perimeter which tapers outwardly from an interior of the pyramidal portion For example, for a helical coil shaped winding, the diameter of the coil tapers outwardly such that the interior part of the loops of the coil has a smaller diameter than outer part of the loops of the coil. Each distal coil also includes a transition segment of the wire between and connecting each distal coil to one or more adjacent distal coils.

The plurality of distal coils is arranged in a pyramidal shape such that each coil is parallel to, and lies in, a different lateral face of the pyramidal shape. For clarity, there is not a distal coil lying in the base of the pyramidal shape. For example, the pyramidal shape may be a tetrahedron having a base with 3 sides connected to an apex with each base side and the apex forming a triangle wherein each triangle defines one of the 3 lateral faces. The body portion described below may form the base portion of the pyramidal shape.

The secondary configuration also has a body portion proximal of the pyramidal portion. The body portion comprises a coil formed from the wire and extending proximally from the pyramidal portion. For example, the body portion may extend proximally from the position of the base of the pyramidal shape.

In another aspect, the pyramidal shape is a polyhedral shape formed of a polygonal base having n number of sides and n number of lateral faces connecting to an apex, such as a tetrahedral shape (triangular base and 3 lateral faces, also referred to as a triangular pyramid), pentahedral shape (quadrilateral base and 4 lateral faces, also referred to as a square or rectangular pyramid), hexahedral shape (pentagonal base and 5 lateral faces, also referred to as a pentagonal pyramid), etc.

In still another aspect, each of the distal coils comprises at least 1⅔ loops or turns (winding of 600°), or from 1⅔ loops to 2⅔ loops (winding of °). In still another feature, the distal coils are overlapping in the transition from one distal coil to an adjacent distal coil. In other words, the transition segment overlaps the coil as it extends from one distal coil to a subsequent, adjacent coil.

In another aspect, the primary configuration comprises an elongate helical coil. The helical coil has an outside diameter (OD) configured to fit within the lumen of a suitable delivery catheter for deploying the catheter. Typically, the elongate helical coil has zero pitch between each loop of the coil which provides the most compact coil. Alternatively, the elongate helical coil may have a non-zero pitch, or even a varying pitch.

In another aspect of the vaso-occlusive device, the wire may be formed from a shape memory material, and the secondary configuration is set by winding the wire on a mandrel and heat treating the wire wound on the mandrel.

In another aspect, each of the distal coils has a coil diameter (the diameter of the inner most loop of each distal coil) between 10 to 90 percent of a diameter of an aneurysm the device is designed to treat, or alternatively, a coil diameter (the diameter of the inner most loop of each distal coil) between 55 to 85 percent of a diameter of an aneurysm the device is designed to treat.

In another aspect of the vaso-occlusive device, the primary shape has a longitudinal length of from 1 to 70 cm.

Methods of making any of the vaso-occlusive devices described herein, and mandrels used to make the vaso-occlusive devices, are also disclosed. In one method of making a vaso-occlusive device using a mandrel, a mandrel for forming the vaso-occlusive device is provided. The mandrel comprises a central, spherical element. A plurality of distal coil posts extend from the central, spherical element. The distal coil posts are spaced angularly around the spherical element. Each distal coil post has a cross-sectional diameter which tapers outwardly as the distal coil post extends away from the spherical element. Each distal coil post also has a longitudinal axis which is oriented such that respective planes perpendicular to each respective longitudinal axis have an intersection which forms a pyramidal shape having an apex distal to the distal coil posts.

The mandrel also has a body post extending from the spherical element. Typically, the body post extends proximally from the spherical element.

A wire having a primary configuration is then wound around the mandrel. The wire may be formed of a shape memory material. The primary configuration may be a configuration of the wire in a constrained condition, such as within a sheath or delivery catheter, and can have any suitable shape, such as a helical coil.

The wire is wound around a first distal coil post of the plurality of distal coil posts in a first direction and winding inward towards the intersection of the first distal coil post and the spherical element and forming at least 360°, or at least 1⅔ first loops (600°) around the first distal coil post. As used herein, a winding "direction" is relative to viewing inwardly along the winding axis toward the position of the attachment of a winding post to the central, spherical element or other central structure. After winding the wire around the first distal coil post, the wire is traversed along the spherical element in a first transition segment to a next distal coil post immediately adjacent to the first distal coil post of the plurality of posts. The wire is then wound around the next distal coil post in a second direction opposite to the first direction starting at the intersection of the next distal coil post and the spherical element forming at least 1⅔ next loops around the next distal coil post, and then traversing along the spherical element in a next transition segment to a subsequent distal coil post immediately adjacent to the preceding distal coil post. The process of winding the wire around each of the distal coil posts in alternating winding directions from the preceding distal coil post and transitioning to the subsequent distal coil post is repeated for each distal coil post. After winding the wire around the last of the distal coil posts, the wire is transitioned along the spherical element to the body post. The wire is then wound around the body post for at least one loop.

In another aspect of the method of making a vaso-occlusive device, the wire as wound around the mandrel is heat treated to set a secondary configuration of the vaso-occlusive device. In still another aspect, the secondary configuration is a relaxed, unconstrained configuration of the wire.

In yet another aspect of the method of making a vaso-occlusive device, the secondary configuration comprises a pyramidal portion and a body portion proximal of the pyramidal portion. The pyramidal portion comprises a plurality of distal coils wound from the wire on respective distal coil posts. Each distal coil comprises a winding forming a closed loop of greater than 360°, or at least 1⅔ loops, wherein the winding has a perimeter which tapers outwardly from an interior of the pyramidal portion. There is also a transition segment of the wire between each distal coil and connecting each distal coil. The plurality of distal coils are arranged in a pyramidal shape such that each coil lies in a different lateral face of the pyramidal shape. The body portion is proximal of the pyramidal portion, and comprises a coil formed from the wire wound on the body post, and extends proximally from the pyramidal portion.

In another aspect of the method, the pyramidal shape is a polyhedral shape formed of a polygonal base having n number of sides and n number of lateral faces connecting to an apex, such as a tetrahedral shape (triangular base and 3 lateral faces, also referred to as a triangular pyramid), pentahedral shape (square/quadrilateral base and 4 lateral faces, also referred to as a square pyramid), hexahedral (pentagonal base and 5 lateral faces, also referred to as a pentagonal pyramid), etc.

In still another aspect, each of the distal coils comprises at least 1⅔ loops or turns, or from 1⅔ loops to 2 loops. In another aspect, each transition segment crosses over at least part of the loops from which the transition segment is transitioning such that the distal coils are overlapping in the transition from one distal coil to an adjacent distal coil. In other words, the transition segment overlaps the coil as it extends from one distal coil to a subsequent, adjacent coil.

In another aspect, the primary configuration comprises an elongate helical coil. The helical coil has an outside diameter (OD) configured to fit within the lumen of a suitable delivery catheter for deploying the catheter. Typically, the elongate helical coil has zero pitch between each loop of the coil which provides the most compact coil. Alternatively, the elongate helical coil may have a non-zero pitch, or even a varying pitch.

In still another aspect of the method, each post may have a cross-sectional diameter which tapers outwardly as the post extends away from the spherical element at an angle between about 5 to 15 degrees, or between about 1 to 30 degrees.

In additional aspects of the device disclosed herein, the vaso-occlusive devices disclosed herein may be a part of a vaso-occlusive system comprising a vaso-occlusive assembly and a delivery assembly. For example, a vaso-occlusive assembly may comprise any of the vaso-occlusive devices described herein, and a pusher member detachably coupled to a proximal end of the vaso-occlusive device. The pusher member is configured to allow a clinician to advance the vaso-occlusive device along a delivery catheter through a patient's vasculature to a target site, such as an aneurysm being treated with the vaso-occlusive device, and to push the vaso-occlusive device out of the distal end of the delivery catheter to deploy the vaso-occlusive device.

In still another aspect, the vaso-occlusive assembly may also include a detachment device detachably coupling the pusher member to the vaso-occlusive device. For example, the detachment device may comprise an electrolytic detachment, mechanical connector, heat activated detachment, dissolving detachment, etc. The delivery assembly may include a delivery catheter into which the vaso-occlusive device may be installed in its compact, delivery configuration. The delivery assembly may also include a guidewire for guiding the delivery catheter to a target implantation site within a patient's vasculature, such as an aneurysm. The guidewire is then be removed, and the vaso-occlusive device is advanced through the delivery catheter to the target implantation site.

In still another aspect of the present disclosure, the devices disclosed herein are not limited to being vaso-occlusive devices, but may be any medical device comprising the same or similar structure of the vaso-occlusive devices disclosed herein. For example, the medical device may be any suitable thrombectomy device, stent retriever, embolic filter, stent delivery system, other implantation device, guidewire, intravascular device, or other medical device.

Methods of deploying any of the vaso-occlusive devices, or other medical devices, disclosed herein into an anatomical cavity, such as an aneurysm, are also disclosed. In one method, the vaso-occlusive device is deployed using a delivery catheter. The delivery catheter is first inserted into the patient's vasculature and is advanced within the vasculature to position the distal end of the delivery catheter at the target insertion site. In this example, the target insertion site is an aneurysm. It is understood that the target insertion site may be any suitable anatomical site or cavity within the vasculature into which the vaso-occlusive device is being deployed. If a guidewire is utilized, the guidewire is first inserted into the patient's vasculature and advanced through the vasculature to the site of the aneurysm. Then, the delivery catheter is advanced along the guidewire to the aneurysm, and then the guidewire is removed.

The vaso-occlusive device is then inserted in its compact, delivery configuration into the delivery catheter and advanced along the delivery catheter until the distal end of the vaso-occlusive device is positioned at the target insertion site. The vaso-occlusive device is then pushed distally out of the delivery catheter, such as by using a pusher-member detachably attached to the proximal end of the vaso-occlusive device. The portions of the vaso-occlusive device in its compact, delivery configuration (e.g., a helical coil) comprising the distal coils of the vaso-occlusive device are first advanced out of the delivery catheter and into the aneurysmal sac. As such portions comprising the distal coils exit the delivery catheter and enter the aneurysm, such portions assume the secondary configuration comprising the distal coils. As the vaso-occlusive device continues to be advanced out of the delivery catheter, the body portion is also advanced into the aneurysmal sac. Once the entire vaso-occlusive device is inserted into the aneurysmal sac, the vaso-occlusive device may be detached from the pusher-member, such as by actuating or activating the detachment device. The vaso-occlusive device in its secondary configuration has a stable shape with inward facing loops. Due to the outwardly tapering diameter, the loops or turns of each of the distal coils are inward facing. In other words, the surface of the loops faces inward toward the geometric interior of the pyramidal shape of the pyramidal portion. The inward facing loops tend to avoid herniating out of the aneurysm during deployment and retention, and the pyramidal configuration of the distal coils also provides shape stability which effectively frames the aneurysm while also exhibiting a soft and pliable structure which avoids imparting excessive forces on the walls which could rupture the aneurysm.

In some cases, a single vaso-occlusive device may be sufficient to fill and occlude the aneurysm. If multiple vaso-occlusive devices are needed, this process may be repeated to deliver a sufficient number of vaso-occlusive devices to fill and occlude the aneurysm.

Accordingly, there is a need for vaso-occlusive devices which can alleviate the issues of herniation during placement and retention and provide effective framing of the aneurysm, and at the same time have a sufficiently soft and pliable structure that will not rupture the aneurysm, especially small, wide-necked aneurysms.

Other and further aspects and features of embodiments of the disclosed inventions will become apparent from the ensuing detailed description in view of the accompanying figures.

BRIEF DESCRIPTION OF THE DRAWINGS

The drawings illustrate the design and utility of various aspects of the devices and methods disclosed herein, in which similar elements are referred to by common reference numerals. It should be noted that the figures are not drawn to scale and that elements of similar structures or functions are represented by like reference numerals throughout the figures. It should also be noted that the figures are only intended to facilitate the description of the various aspects of the disclosed technology. They are not intended as an exhaustive description of the technology or as a limitation on the scope of the technology, which is defined only by the appended claims and their equivalents. In addition, an illustrated example of the disclosed technology need not have all the aspects or advantages shown or described herein. An aspect or an advantage described in conjunction with a particular example of the disclosed technology is not necessarily limited to that example and can be practiced in any other examples even if not so illustrated. In order to better appreciate how the above-recited and other advantages and objects of the present technology are obtained, a more particular description of the present technology briefly described above will be rendered by reference to specific examples thereof, which are illustrated in the accompanying drawings. With the understanding that these drawings and corresponding description depict only illustrative examples of the disclosed technology and are not therefore to be considered limiting of its scope, the technology will be described and explained with additional specificity and detail through the use of the accompanying drawings in which:

DETAILED DESCRIPTION

Figure 1:
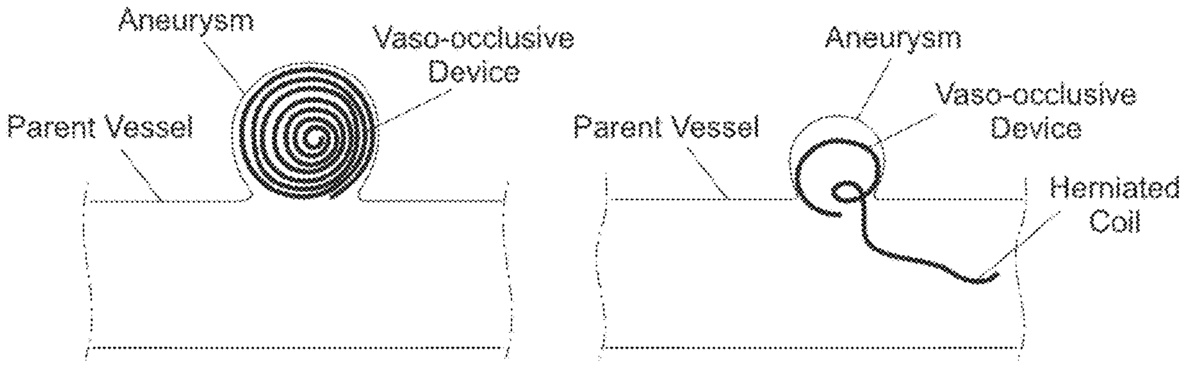
FIG. 1 is a side, cross-sectional view of a delivery catheter deploying a vaso-occlusive device in which the vaso-occlusive device is herniating.
Figure 2:
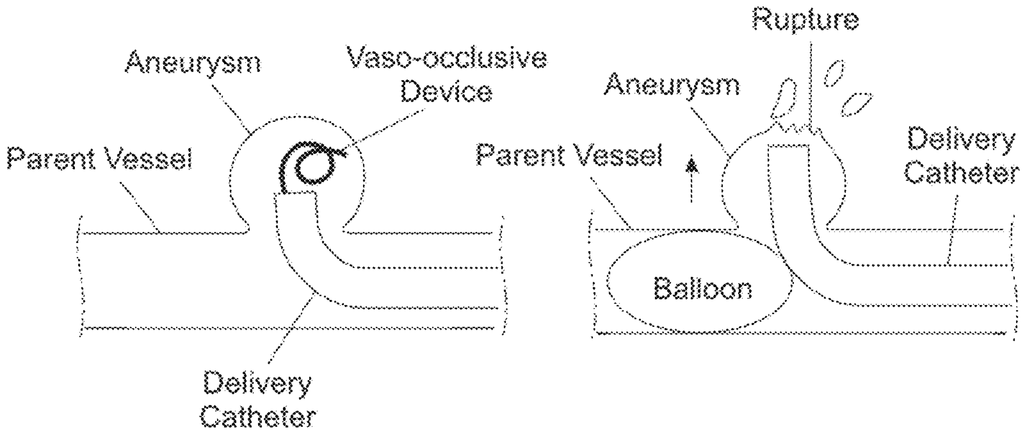
FIG. 2 is cross-sectional, side view of a delivery catheter deploying a vaso-occlusive device and a balloon activated catheter used in a jailing technique.
Figure 3:
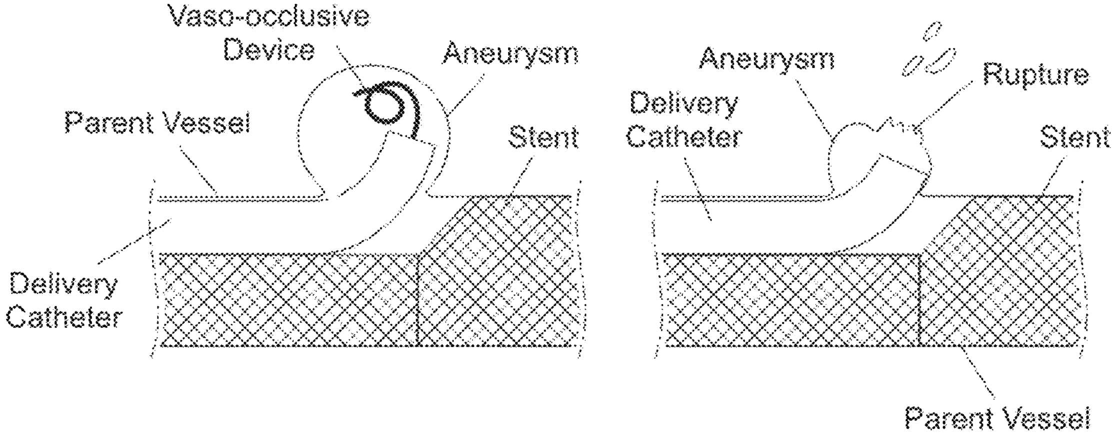
FIG. 3 is a cross-sectional, side view of a delivery catheter deploying a vaso-occlusive device and a stent used in a jailing technique.
Figure 4:
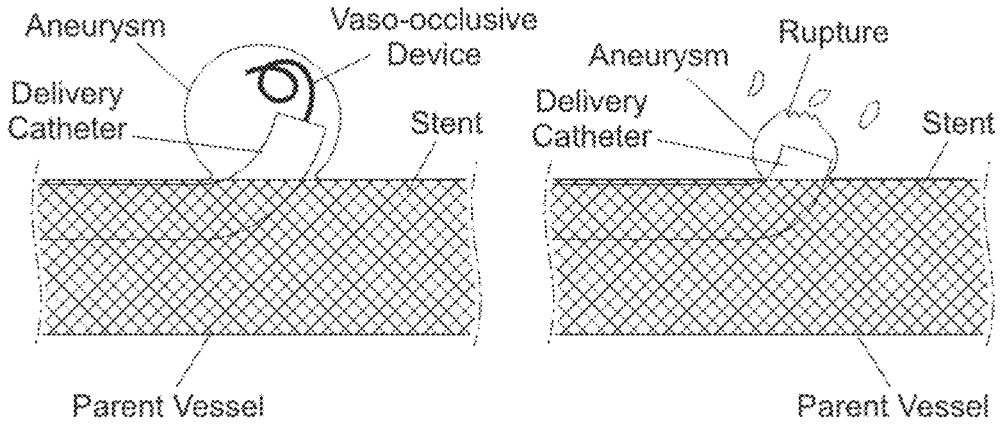
FIG. 4 is a cross-sectional, side view of a delivery catheter deploying a vaso-occlusive device and a stent used in a recrossing technique.
Figure 5:
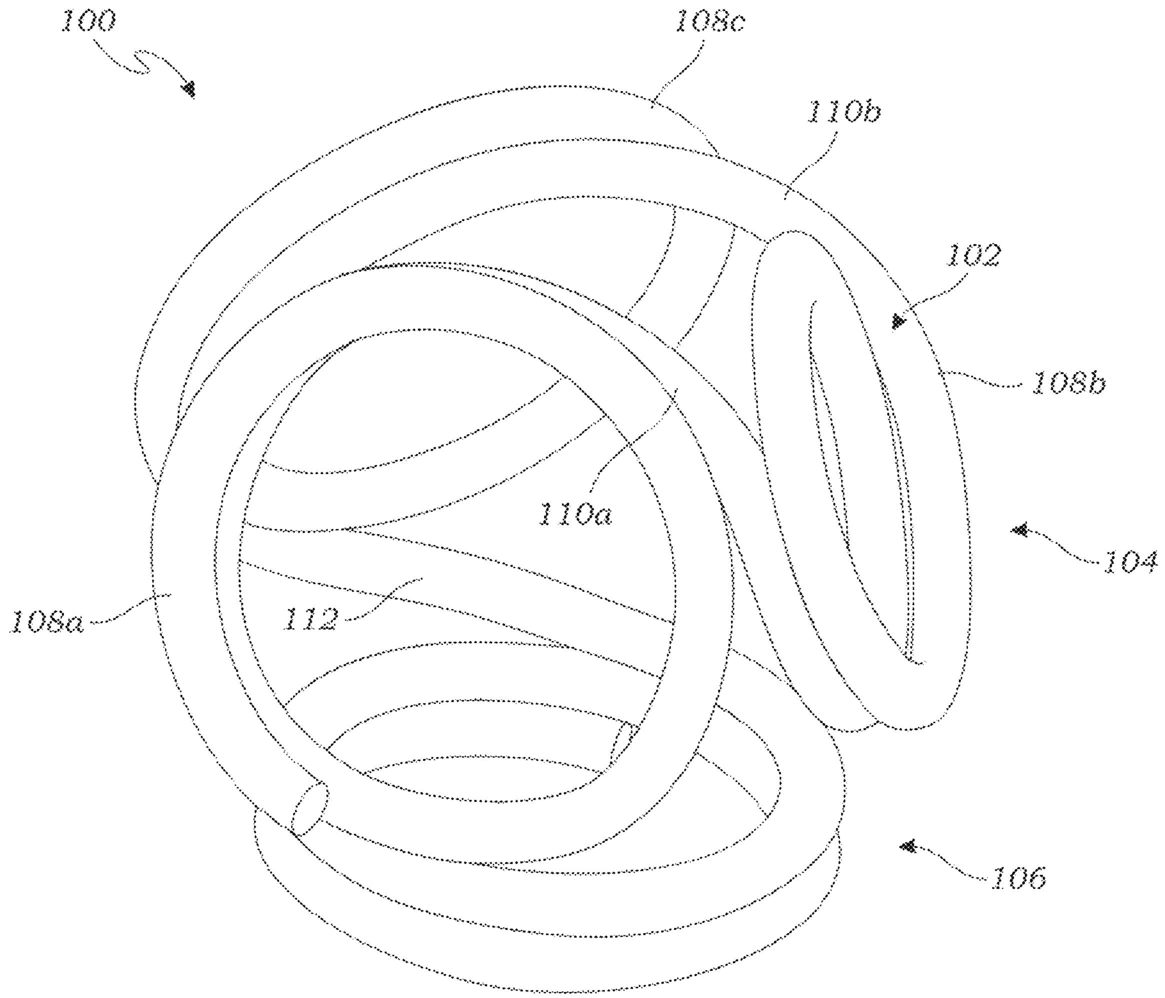
FIG. 5 is a side, perspective view of a vaso-occlusive device in a relaxed, deployed configuration.

Referring to FIG. 5, an example of a vaso-occlusive device 100, as disclosed herein, is illustrated. FIG. 5 depicts the vaso-occlusive device 100 in its secondary configuration in a relaxed, unconstrained condition. In other words, FIG. 5 shows the vaso-occlusive device 100 when there are no external forces exerting on the vaso-occlusive device 100. The secondary configuration of the vaso-occlusive device 100 has a distal pyramidal portion 104 and a proximal body portion 106, such that the distal pyramidal portion 104 is distal to the proximal body portion 106. The terms "distal" and "proximal" as used herein are relative to the vaso-occlusive device 100 as it is intended to be deployed, wherein the term "distal" refers to being situated toward the end of the device 100 which is inserted first, and "proximal" refers to being situated toward the end of the device 100 which is inserted last.

The vaso-occlusive 100 comprises a wire 102 having a primary configuration in a constrained configuration. For instance, the constrained configuration may be an elongate, helical coil when the wire 102 is constrained within a delivery catheter (see FIG. 14A). Typically, the primary shape has a longitudinal length between 1 cm to 70 cm. The wire 102 is made from any suitable material, but typically comprises a radiopaque, shape memory material, such as the platinum group metals, including platinum, rhodium, palladium, and rhenium, as well as tungsten, gold, silver, tantalum, and alloys of these metals.

Figure 6:
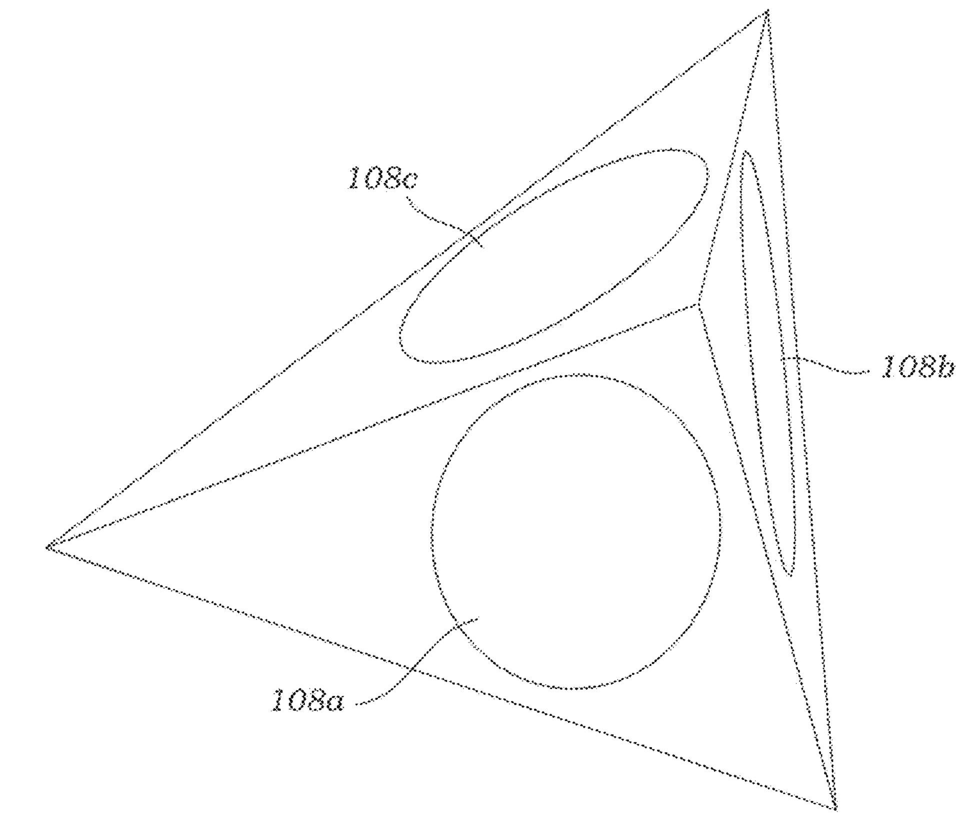
FIG. 6 is a top perspective view of a simplification of the intersecting planes of the 3 distal coils of FIG. 5 forming the pyramidal portion of the vaso-occlusive device in the shape of a triangular pyramid.
Figure 7:
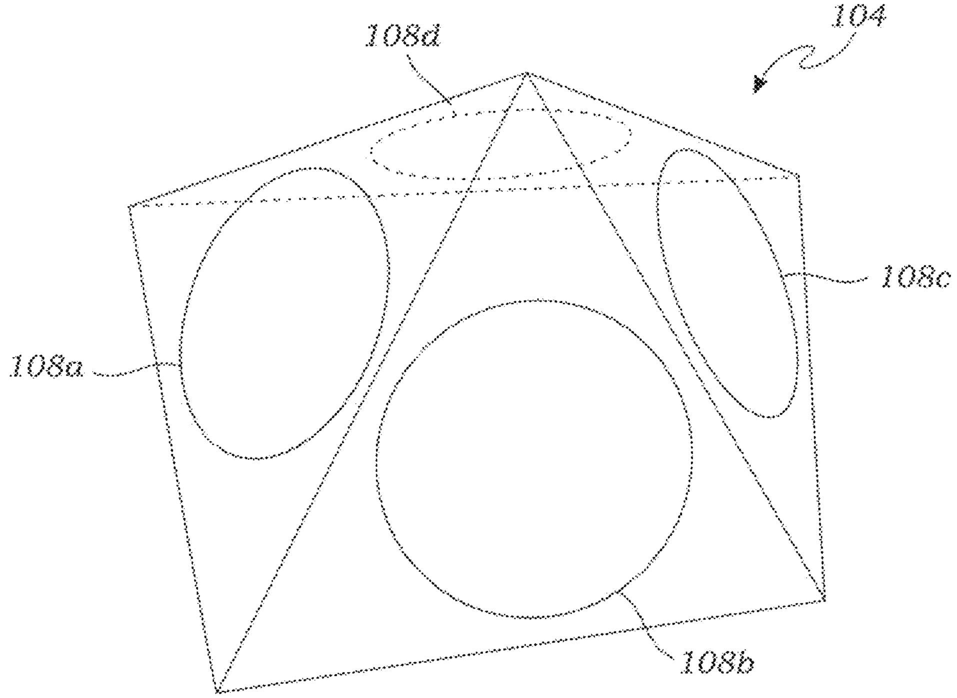
FIG. 7 is a top perspective view of a simplification of the intersecting planes of 4 distal coils forming the pyramidal portion of a vaso-occlusive device in the shape of a square pyramid.
Figure 14A:
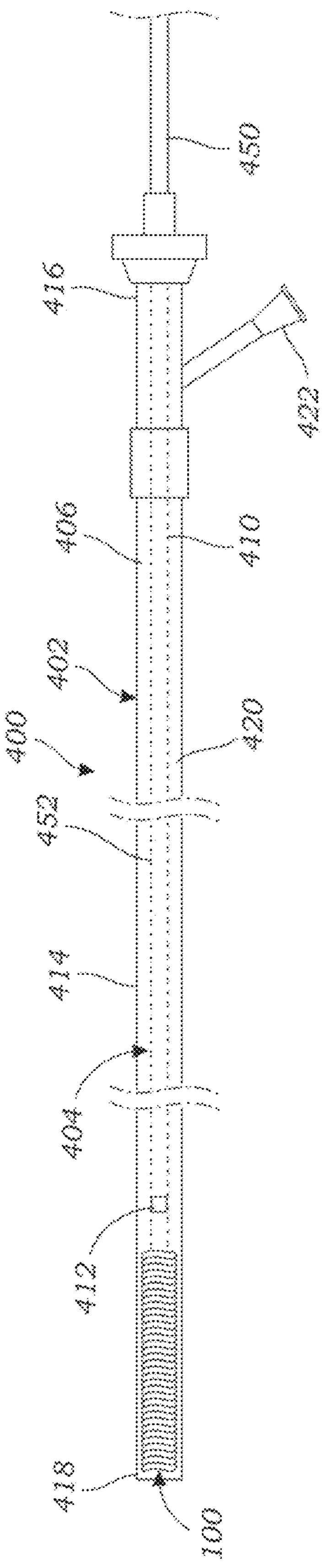
FIG. 14A is a cross-sectional side view of a vaso-occlusive system including the vaso-occlusive device of FIG. 5 in its restrained, delivery configuration within a delivery catheter.

The pyramidal portion 104 in the secondary configuration of the vaso-occlusive device 100 is formed by a distal portion of the vaso-occlusive device 100 in its primary configuration (see FIG. 14A). The pyramidal portion 104 includes a plurality of distal coils 108 wound from the wire 102. In the illustrated example of FIG. 5, the pyramidal portion 104 includes three distal coils 108*a*, 108*b*, and 108*c*, arranged to form a pyramidal shape having three lateral faces, also referred to as a triangular pyramid as the base (the distal coils 108 do not include a distal coil at the base of the pyramidal shape) is a triangle, wherein a respective coil 108 lies in each lateral face of the triangular pyramid. The respective planes in which each distal coil 108 lies are non-parallel and intersect with each other. As depicted in FIG. 6, a simplification of the intersecting planes of the distal coils 108 forms a tetrahedral, more specifically, a triangular pyramid. The vaso-occlusive device 100 of FIG. 5 is an example, and is not limited to distal coils 108 forming a triangular pyramid shape, but may be other suitable pyramidal shapes, such as n number of distal coils 108 forming a pyramid having a polygonal base having n number of sides and n number of lateral faces connecting to an apex. For instance, the vaso-occlusive device 100 may have distal coils 108 in each lateral face of a pyramidal shape which may be a square pyramid having a square base and 4 lateral faces, a quadrilateral pyramid having a quadrilateral base and 4 lateral faces, a pentagonal pyramid having a pentagonal base and 5 lateral faces, etc. As depicted in FIG. 7, the pyramidal portion 104 may have 4 distal coils 108 in each lateral face arranged to form a square pyramid having a square base and 4 lateral faces.

Turning back to FIG. 5, each distal coil 108 includes a winding forming a closed loop of greater than 360°, i.e., at least a complete, closed loop. In the illustrated vaso-occlusive device 100, each distal coil 108 includes a winding of 1⅔ loops (also referred to as "turns"), which is equivalent to a winding of 600°. Alternatively, each distal coil 108 may have at least 1⅔ turns, or between 1⅔ turns (600°) and 2 turns (720°).

Figure 8:
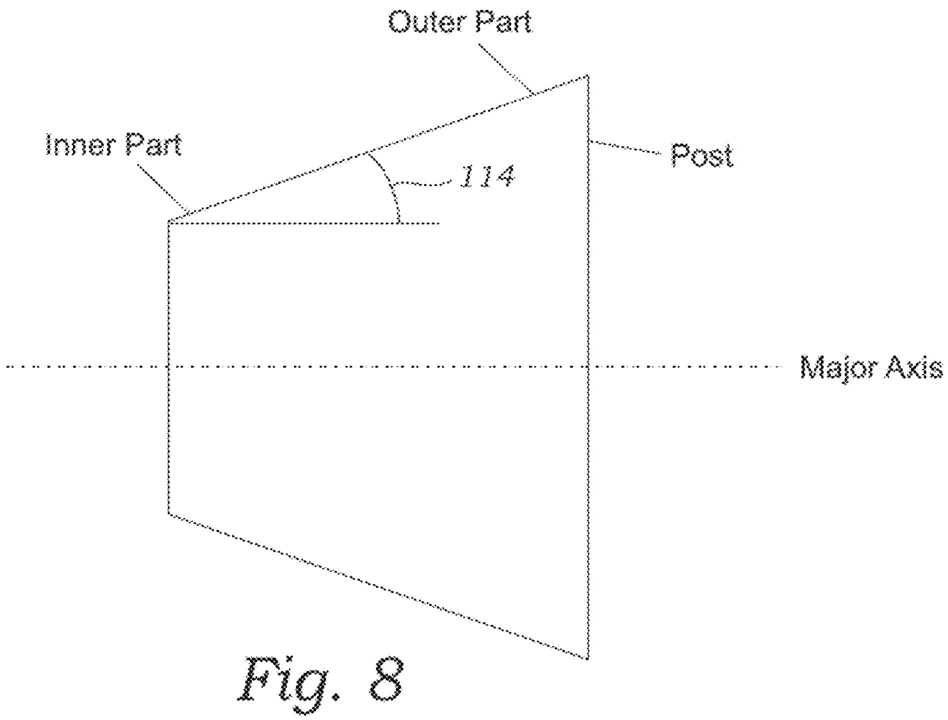
FIG. 8 is a side view of distal coil post for forming the distal coils illustrating the taper angle for the loops of a coil.

The winding of each of the distal coils 108 also has a width which tapers outwardly from a reference point of the interior of the pyramidal portion. In the case of a helical coil as depicted in the example of FIG. 5, the width of each distal coil 108 is the diameter of the coil. If the distal coils 108 are wound in a different shape, such as a square, pentagon, or other polygonal or curved shape, the width may be an average width, such an average of the maximum and minimum width drawn through the geometric center of the shape. Turning the example of FIG. 5, the diameter of each distal coil 108 tapers such that the diameter of the outer part of the coil 108 is larger than the diameter of the inner part of the coil 108. This may be better explained with reference to a cross-section of a cylindrical post upon which the distal coil 108 are wound, as shown in FIG. 8. The post has a diameter which tapers outwardly from the inner part of the post to the outer part of the post, as depicted in FIG. 8. The angle 114 of the post taper defines the angle of the taper of the distal coil 108 in the secondary configuration of the vaso-occlusive device 100. Due to the outwardly tapering diameter, the loops or turns of each of the distal coils 108 is inward facing. In other words, the surface of the loops faces inward toward the geometric interior of the pyramidal shape of the pyramidal portion 104.

Each of the distal coils 108 has a diameter (defined as the diameter of the inner most loop of each distal coil 108)

between 10 to 90 percent of a diameter of an aneurysm the vaso-occlusive device 100 is designed to treat. Alternatively, the diameter of each distal coil 108 may be between 55 to 85 percent of a diameter of an aneurysm the vaso-occlusive device 100 is designed to treat.

Figure 9:
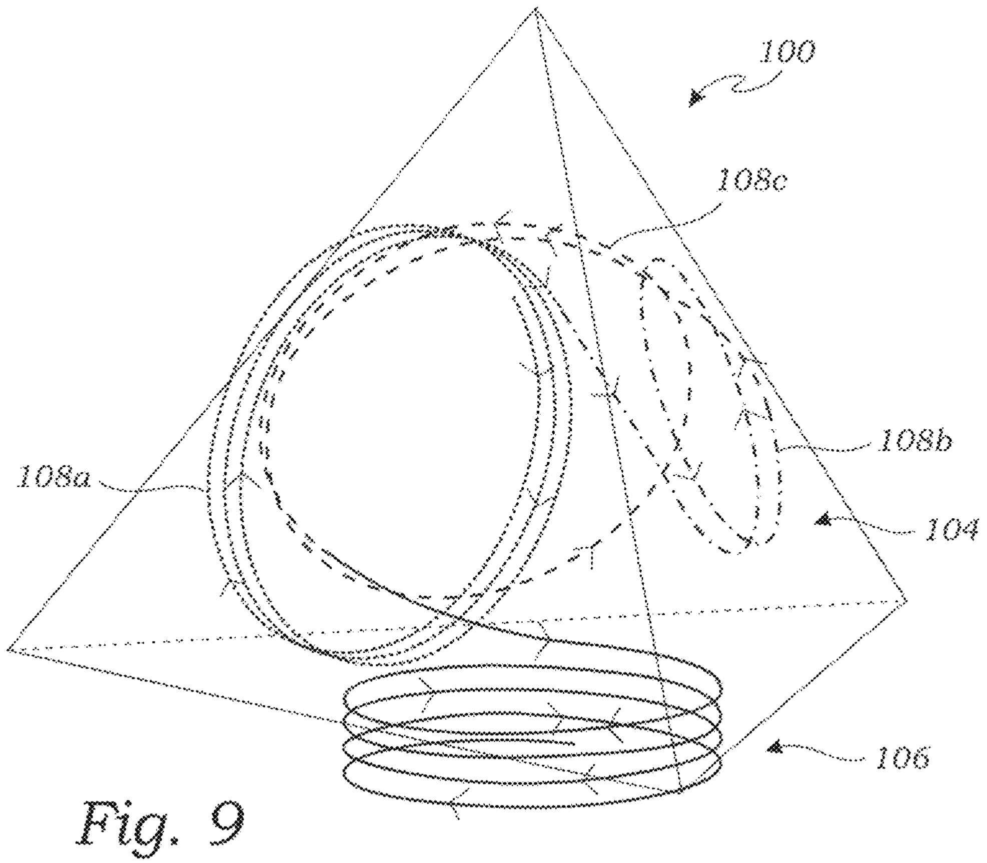
FIG. 9 is a side, perspective view of an example of an alternative pyramidal portion of the vaso-occlusive device of FIG. 5 in which the distal coils have varying diameters and varying numbers of turns.

In an alternative design of the vaso-occlusive device 100, the distal coils 108 may have differing diameters and/or differing numbers of turns of the wire 102, as illustrated in FIG. 9. As shown in FIG. 9, the first distal coil 108*a* has a larger diameter and more turns of the wire 102 (3 turns, i.e., 1080°) than the second distal coil 108*b* which has 1⅔ turns (600°). The third distal coil 108*c* also has a larger diameter than the second distal coil 108*b* (same diameter as the first distal coil 108*a* and 1⅔ turns (600°).

The pyramidal portion 104 also includes a respective transition segment 110 of the wire 102 which is between and connecting each adjacent distal coil 108 to each other. Each transition segment 110 extends from the ending of one distal coil 108 to the beginning of the subsequent distal coil 108. Hence, the transition segment 110*a* extends from the ending of the distal coil 108*a* to the beginning of the distal coil 108*b*, and the transition segment 110*b* extends from the ending of the distal coil 108 to the beginning of the distal coil 108*c*. There is also a transition segment 112 from the ending of the last distal coil 108*c* winding to the beginning of the body portion 106.

The body portion 106 comprises a winding of the wire 102 which extends proximally from the pyramidal shape 104. The body portion 106 may extend from the imaginary base of the pyramidal shape of the pyramidal portion 104. In the illustrated example of FIG. 5, the body portion 106 is a helical coil extending proximally from the pyramidal portion 104. The body portion 106 may have a constant diameter, or alternatively, the body portion 106 may have a diameter which tapers outwardly or inwardly as it extends from the proximally from the pyramidal portion 104. The body portion 106 comprises at least one full loop of the wire 102. The body portion 106 does not have a maximum degree of winding and may include any suitable number of turns, such as between 1 and 20 turns. The body portion 106 depicted in FIG. 5 has about 2 full turns of the wire 102. The body portion 106 depicted in FIG. 9 has about 4 full turns of the wire 102.

Figure 10:
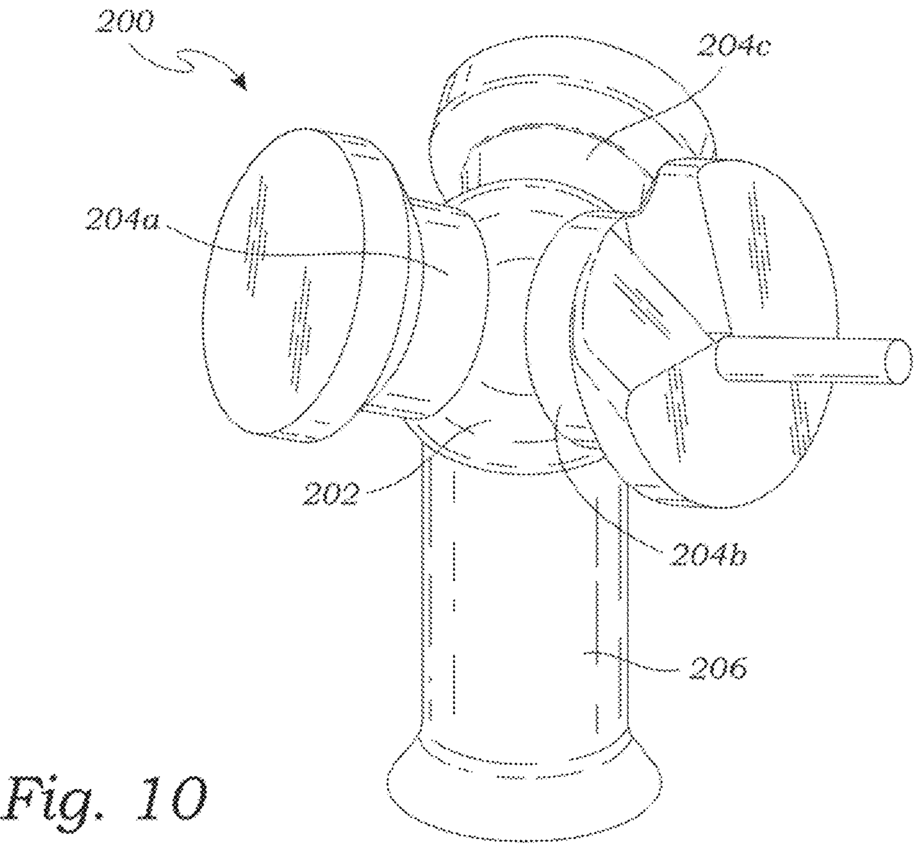
FIG. 10 is a side, perspective view of an exemplary mandrel for making the vaso-occlusive device of FIG. 5.

Turning to FIG. 10, an exemplary mandrel 200 for making the vaso-occlusive device 100 using a method 300 (described below) is illustrated. The mandrel 200 is used to wind the wire 102 around to form the secondary configuration of the vaso-occlusive device 100. The mandrel 200 is configured to form a vaso-occlusive device 100 comprising a pyramidal portion 104 having a triangular pyramid shape.

The mandrel 200 has a central, spherical element 202. A plurality of distal coil posts 204 extend outwardly from the central spherical element 202. The distal coil posts 204 are configured to form the distal coils 108 of the vaso-occlusive device 100. The distal coil posts 204 are spaced angularly around the spherical element 202. In the depicted mandrel 200, the distal coil posts 204 are evenly spaced such that a respective longitudinal axis of each distal coil is evenly, angularly spaced around the spherical element 202. Accordingly, in the case of three distal coil posts 204, the distal coil posts 204 are spaced apart by 120°.

Each distal coil post 204 has a cross-sectional diameter which tapers outwardly as the distal coil post 204 extends away from the spherical element 202, as shown in FIG. 8 which shows a side view of one of the distal coil posts 204. The angle 114 of the taper of the distal coil posts 204 is the same as the taper of the distal coils 108, described herein. The longitudinal axis of each distal coil post 204 is also canted distally such that respective planes perpendicular to each respective longitudinal axis are non-parallel and non-perpendicular and the planes have an intersection which forms a pyramidal shape having an apex distal to the distal coil posts 204.

The mandrel 200 also has a body post 206 extending from the spherical element 202. The body post 206 is configured to form the body portion 106 of the vaso-occlusive device 100. In the illustrated example of FIG. 10, the body post 206 extends proximally from the spherical element 202 and perpendicular to the base of the pyramidal shape. The body post 206 may be a cylinder having a constant diameter, or alternatively, the body post 206 may taper outwardly or inwardly as it extends from the spherical element 202.

Figure 11:
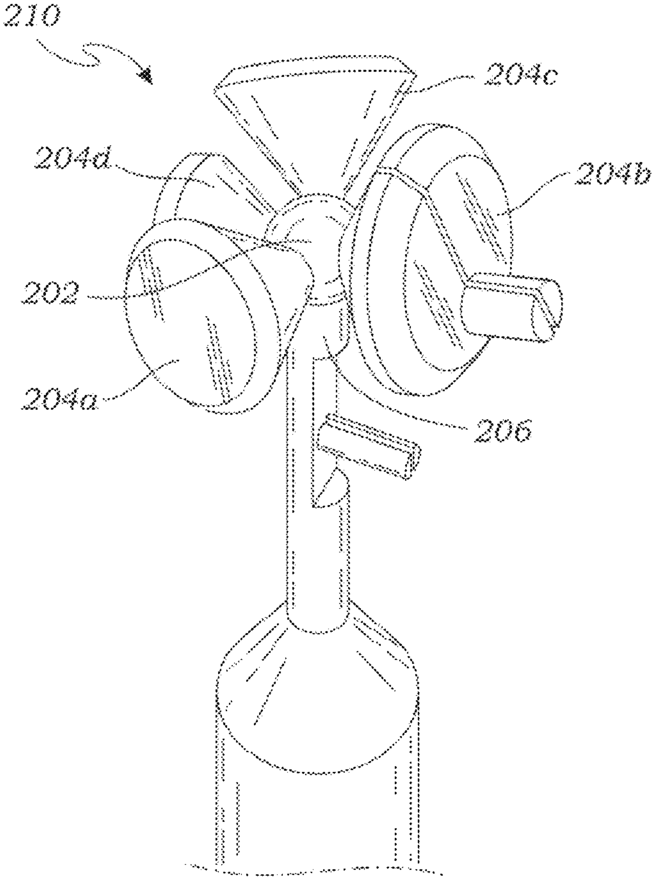
FIG. 11 is a side, perspective view of an exemplary mandrel for making a vaso-occlusive device having 4 distal coils forming the pyramidal portion in the shape of a square pyramid.

With the assistance of the present description, one of ordinary skill in the art would appreciate how to modify the mandrel 200 to be configured to make a vaso-occlusive device 100 comprising a pyramidal portion 104 having the other pyramid shapes disclosed herein. For instance, FIG. 11 shows a mandrel 210 which is configured to make a vaso-occlusive device 100 comprising a pyramidal portion 104 having a square pyramid shape. The mandrel 210 is same or substantially similar to the mandrel 200, except that the mandrel 210 has four distal coil posts 204 evenly, angularly spaced around the central, spherical member 202.

Figure 12A:
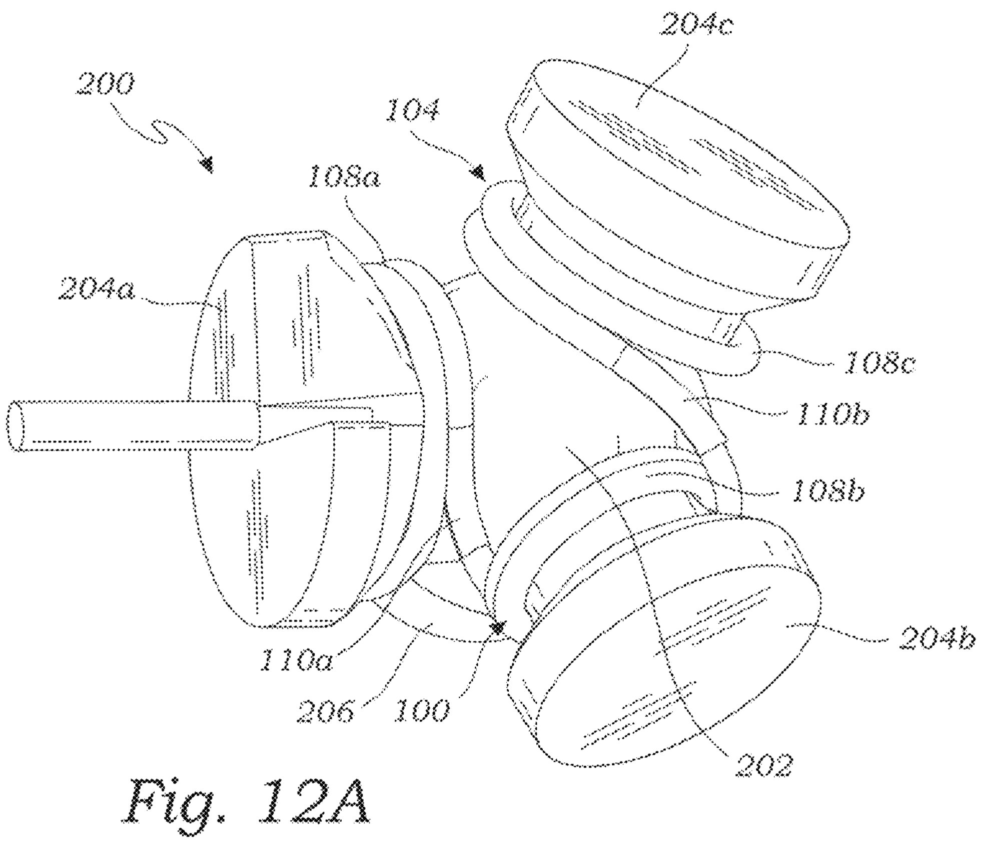
FIG. 12A is a top, perspective view of the mandrel of FIG. 10 with a wire wound around the mandrel to make the vaso-occlusive device of FIG. 5.
Figure 12B:
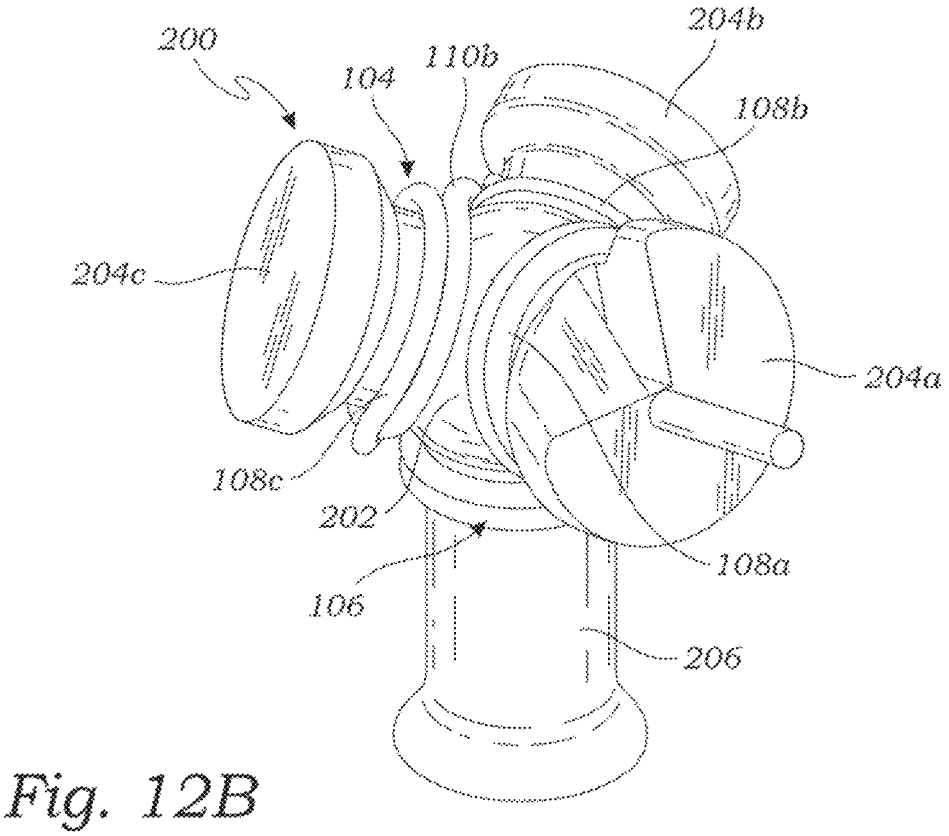
FIG. 12B is a side, perspective view of the mandrel of FIG. 12A with the wire wound around the mandrel to make the vaso-occlusive device of FIG. 5.
Figure 13:
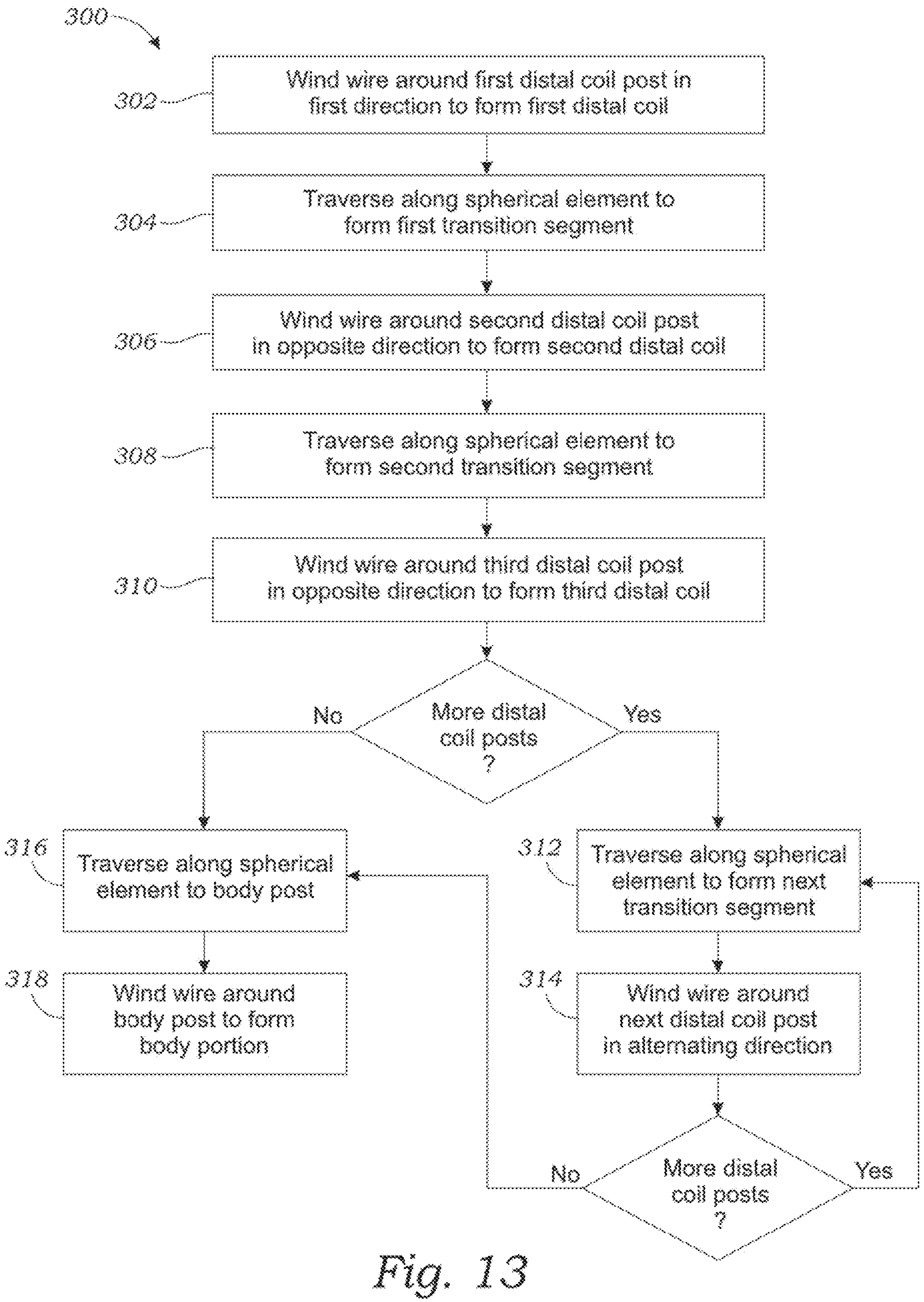
FIG. 13 is a flow chart showing a method of making the vaso-occlusive devices described herein using the mandrels described herein.

Turning to the illustrations in FIGS. 12A-12B and the flow chart of FIG. 13, an exemplary method 300 of making a vaso-occlusive device 100 using the mandrel 200 will now be described. A wire 102 having a primary configuration is wound around the mandrel 300. As described herein, the wire 102 may be formed of a shape memory material, and the primary configuration may be a configuration of the wire 102 in a constrained condition, such as within a sheath or delivery catheter. The primary configuration may have any suitable shape, such as a helical coil.

At step 302, the wire 102 is first wound around the first distal coil post 108*a* in a first direction starting on the first distal coil post 108*a* post and towards the intersection of the first distal coil post 204*a*, and the spherical element 202. Subsequent windings start at the intersection of the post 204 and spherical element 202 and wind away from the spherical element 202. As used herein, a winding "direction" is relative to viewing inwardly along the winding axis toward the position of the attachment of a winding post to the central, spherical element or other central structure. Thus, the "first direction" as shown in the example of FIGS. 12A and 12B is a clockwise direction. The wire 102 is wound around the first distal coil post 204*a* to form the desired degree of winding for the first distal coil 108*a*, as described herein.

After winding the wire 102 around the first distal coil post 204*a*, at step 304, the wire 102 is traversed along the spherical element 202 forming the first transition segment 110*a* to the second distal coil post 108*b* immediately adjacent to the first distal coil post 108*a*. At step 306, the wire 102 is wound around the second distal coil post 204*b* in a second direction opposite to the first direction (counter-clockwise as shown in the example of FIGS. 12A-12B) starting at the intersection of the second distal coil post 204*b* and the spherical element 202. The wire 102 is wound around the second distal coil post 204*b* to form the desired degree of winding for the second distal coil 108*a*, as described herein.

After winding the wire 102 around the second distal coil post 204*b*, at step 308, the wire 102 is traversed along the spherical element 202 forming the second transition segment

110*a* to the third distal coil post 204*c* immediately adjacent to the second distal coil post 204*b*. At step 310, the wire 102 is wound around the third distal coil post 204*c* in a third direction opposite to the second direction (clockwise as shown in the example of FIGS. 12A-12B) starting at the intersection of the third distal coil post 204*c* and the spherical element 202. The wire 102 is wound around the third distal coil post 204*c* to form the desired degree of winding for the third distal coil 108*c*, as described herein.

Looking at a post 204 that is being wound axially along the axis of rotation, each of the three other posts 204 can be described at ⅓ rotations as the coil is being wound. Accordingly, a winding of 1⅔ loops or turns (i.e., 600°) means that as the wire 102 is wound around the post 204, each of the other posts 204, 206 that are passed represents and winding of ⅓ of a loop or turn. Hence, a winding of 1⅔ loops passes the three other posts 204, 206 once, and then re-passes 2 of the 3 other posts 204, 206 for a total of 1⅔ loops. A winding of about 2⅔ (960°) passes each of the other posts 204, 206 twice and then passes the next 2 posts a third time. The winding of a full loop (360°), or multiple full loops (360°×a whole number) plus another ⅔ of a loop, positions the end of a coil 108 to wind in the opposite direction on the next adjacent post 108. One of ordinary skill in the art will immediately understand how to determine the correct amount of loops for a mandrel having more than 3 posts 108, such as 4 posts 108, 5 posts 108, etc.

In the case of a mandrel 200 having more than 3 distal coil posts 204, at step 312, the wire is 102 traversed along the spherical element 202 in a next transition segment 110 to a next distal coil post 204 immediately adjacent to the preceding distal coil post 204. At step 314, the wire is wound around the next distal coil post 204 to form the next distal coil 108, and steps 312-314 are repeated for each additional distal coil post 204. After winding the wire around the last of the distal coil posts 204, at step 316, the wire 102 is transitioned along the spherical element 202 to the body post 206. At step 318, the wire 102 is wound around the body post 206 to form the desired degree of winding for the body portion 106, as described herein.

At step 320, the wire 102 is heat treated to set the secondary configuration of the vaso-occlusive device 100 as wound on the mandrel 200. The wire 102 may then be removed from the mandrel 200, and the wire 102 will take on the secondary configuration having the secondary shape as wound on the mandrel in its relaxed, unconstrained condition.

Accordingly, disclosed herein are a vaso-occlusive device 100, and method 300 for making it, which alleviates the issues of herniation during placement and retention and provides effective framing of the aneurysm, while at the same time have a sufficiently soft and pliable structure that will not rupture the aneurysm, especially small and/or wide-necked aneurysms. The pyramidal shape of the distal coils 108 of vaso-occlusive device 100 has in inherent ability to effectively dissipates forces applied to its apexes, thereby reducing the risk of imparting excessive forces on the walls of the aneurysm which could rupture the aneurysm, including small and/or wide-necked aneurysms. Furthermore, the distal coils are tapered to be inwardly facing and comprise full, closed loops and crossing, overlapping segments which fold more tightly than open loops when deployed in an aneurysm thereby reducing the risk of herniation during placement and retention. At the same time, shape stability is not compromised because of the inherent ability of the pyramidal shape to dissipate forces applied at the apexes. Furthermore, as illustrated in FIG. 5, the pyramidal shaped vaso-occlusive device 100 is more compact than a cube shaped vaso-occlusive device having 8 coils forming the 8 sides of a cube. In other words, the volume of the pyramidal shaped vaso-occlusive device 100 has a smaller volume than a cube. In addition, the distal coils 108 of the vaso-occlusive device 100 have a smaller diameter than the coils of a cube shaped vaso-occlusive device having the same or substantially same overall height as the vaso-occlusive device 100. This is because the diameter of each of the distal coils 108 is smaller than the overall height of the vaso-occlusive device 100 (e.g., 2.4 mm diameter of the distal coils vs. a 3.2 mm overall height of the vaso-occlusive device 100. Whereas, the diameter of the coils of a cube shaped vaso-occlusive device extend the full height of the entire vaso-occlusive device (the height being the length of any one of the sides of the cube shaped vaso-occlusive device.

Figure 14B:
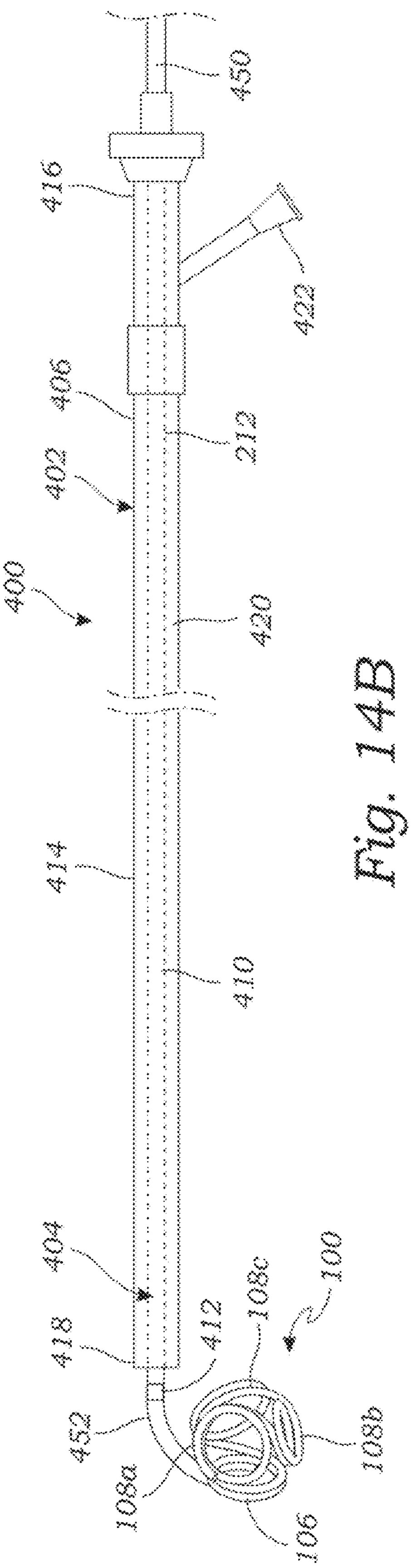
FIG. 14B is a cross-sectional, side view of the vaso-occlusive system of FIG. 14A with the vaso-occlusive device deployed out of the delivery catheter and in its expanded, deployed configuration.
Figure 15:
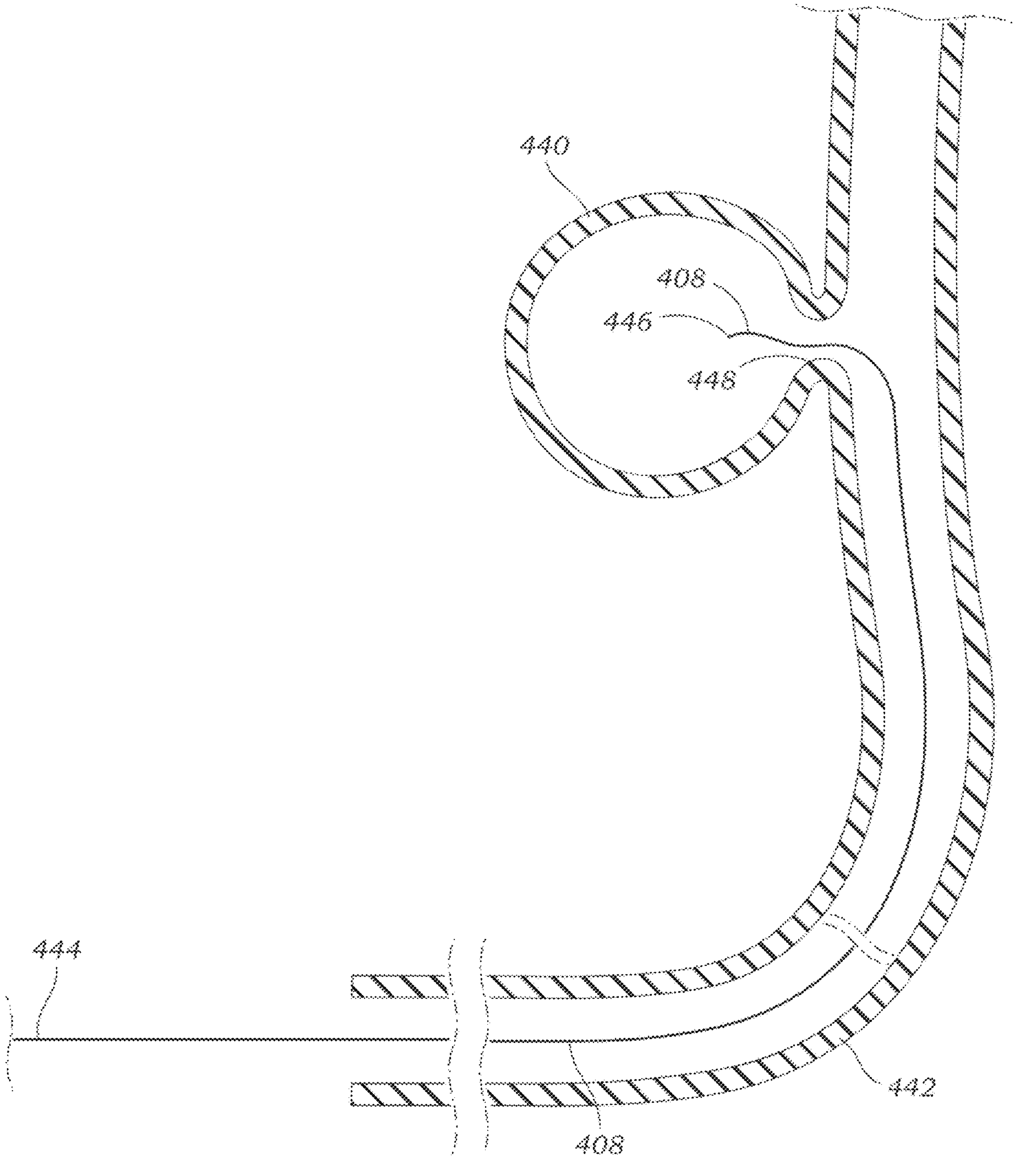
FIG. 15 a cross-sectional, side view depicting a guidewire advanced into a portion of a patient's vasculature to the location of an aneurysm.
Figure 16:
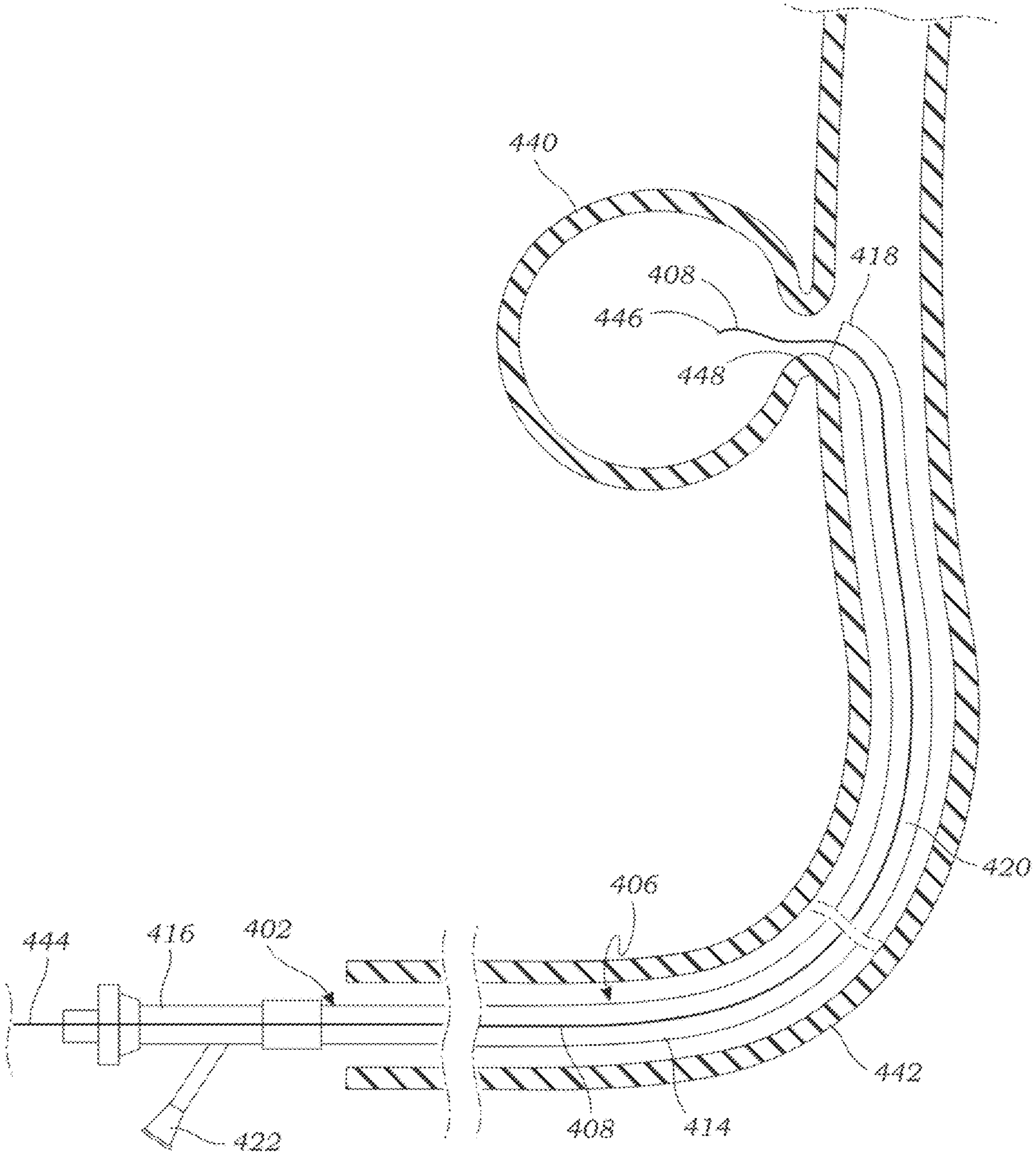
FIG. 16 is a cross-sectional, side view depicting the guidewire and patient's vasculature of FIG. 15 with a delivery catheter advanced over the guidewire.

Turning to FIGS. 14A and 14B, the vaso-occlusive device 100 may also be a component of a vaso-occlusive system 400 which can be used to deploy the vaso-occlusive device 100 into a body cavity, such as an aneurysm 440 (see FIGS. 15-18). The vaso-occlusive system 400 comprises a delivery assembly 402 and a vaso-occlusive assembly 404. As shown in FIGS. 15 and 16, the delivery assembly 402 may include a delivery catheter 406 and an optional guidewire 408. The vaso-occlusive assembly 404 comprises a vaso-occlusive device 100 and a pusher member 410 detachably coupled to the vaso-occlusive device 100 via a detachment device or junction 412. FIG. 14A shows the vaso-occlusive assembly 404 after it has been slidably disposed within the delivery catheter 406 such that the vaso-occlusive device 100 is in its compact, delivery configuration.

The delivery catheter 406 is typically an elongated, flexible tube, and can be, for example, a microcatheter or the like. The delivery catheter 406 comprises an elongate sheath body 414 having a proximal portion 416, a distal portion 418 and a lumen 420 extending from the proximal portion 416 to the distal portion 418. The proximal portion 416 of the delivery catheter 406 typically remains outside of the patient and accessible to the clinician when the vaso-occlusive system 400 is used, while the distal portion 418 is sized and dimensioned to reach remote locations of a patient's vasculature and is configured to deliver the vaso-occlusive device 100 to a body cavity such as an aneurysm. The delivery catheter 406 may also have one or more ports 422 in fluid communication with the lumen 420 for introducing into, or removing fluids from, the sheath body 414. The sheath body 414 may be composed of suitable polymeric materials, metals and/or alloys, such as polyethylene, stainless steel or other suitable biocompatible materials or combinations thereof. In some instances, the proximal portion 416 may include a reinforcement layer, such as a braided layer or coiled layer to enhance the pushability of the sheath body 414. The sheath body 414 may include a transition region between the proximal portion 416 and the distal portion 418.

The vaso-occlusive device 100 may be any of the vaso-occlusive device 100 disclosed herein, having any one or more of the features and aspects described herein.

The vaso-occlusive assembly 404 also comprises a pusher member 410. The pusher member 410 is configured to be slidably received within the lumen 420 of the delivery catheter 406. The pusher member 410 has a proximal portion 450, which typically extends proximal of the proximal portion 416 of the delivery catheter 406, and a distal portion 452 which is detachably coupled to the proximal end of the vaso-occlusive device 100 via the detachment device 412. The pusher member 410 may be a coil, wire, tendon, conventional guidewire, torqueable cable tube, hypotube, or the like, having a sufficient columnar strength to permit pushing of the vaso-occlusive device 100 out through distal end 418 of the delivery catheter 406 and into the aneurysmal sac 440 (see FIGS. 17 and 18).

The detachment device 412 provides a detachable connection between the pusher member 410 and the vaso-occlusive device 100. The detachment device 412 may comprise an electrolytically detachment, mechanical connector, heat activated detachment, dissolving detachment, or other mechanical, thermal and hydraulic mechanism. For instance, the detachment device 412 may be an electrolytically degradable segment for electrolytically decoupling the vaso-occlusive device 100 from the pusher member 410.

As shown in FIGS. 15 and 16, the optional guidewire 408 of the delivery assembly 402 has a proximal end 444 and a distal end 446. As shown in FIG. 16, after the guidewire 408 is positioned within the patient's vasculature 442 with the distal end 446 located at the target insertion site, the delivery catheter 406 is advanced over the guidewire 408 with the guidewire 408 disposed within the lumen 420 of the delivery catheter 406. In a "rapid-exchange" configuration of the delivery catheter 406 and guidewire 408, the guidewire 408 extends through only a distal portion of the delivery catheter 406, such as a rapid-exchange lumen. The guidewire 408 is typically used by first advancing the guidewire 408 through the patient's vasculature to the target insertion site (e.g., the neck 448 of an aneurysm to be filled by the vaso-occlusive device 100, see FIGS. 15-18), and then advancing the delivery catheter 406 over the guidewire 408 to the target insertion site.

Turning to FIGS. 15-19, an exemplary method 500 of using the vaso-occlusive system 200 to deploy the vaso-occlusive device 100 into an anatomical cavity will now be described. The method 500 will be described with respect to deploying the vaso-occlusive device 100 into an aneurysmal sac 440, as an example. However, the method 500 is not limited to deploying the vaso-occlusive device 100 into an aneurysmal sac 440, but may be used to deploy the vaso-occlusive device 100, or other medical device as disclosed herein, into any suitable anatomical cavity which is accessible via a patient's vasculature. Referring to the flow chart of FIG. 19 and FIG. 16, at step 502, the guidewire 408 is inserted into the patient's vasculature 442 and is advanced to the target insertion site, namely the aneurysmal sac 440. As described herein, the use of the guidewire 408 is optional, and is not required in the method 500 of using the vaso-occlusive system 200 to deploy the vaso-occlusive device 100.

Figure 17:
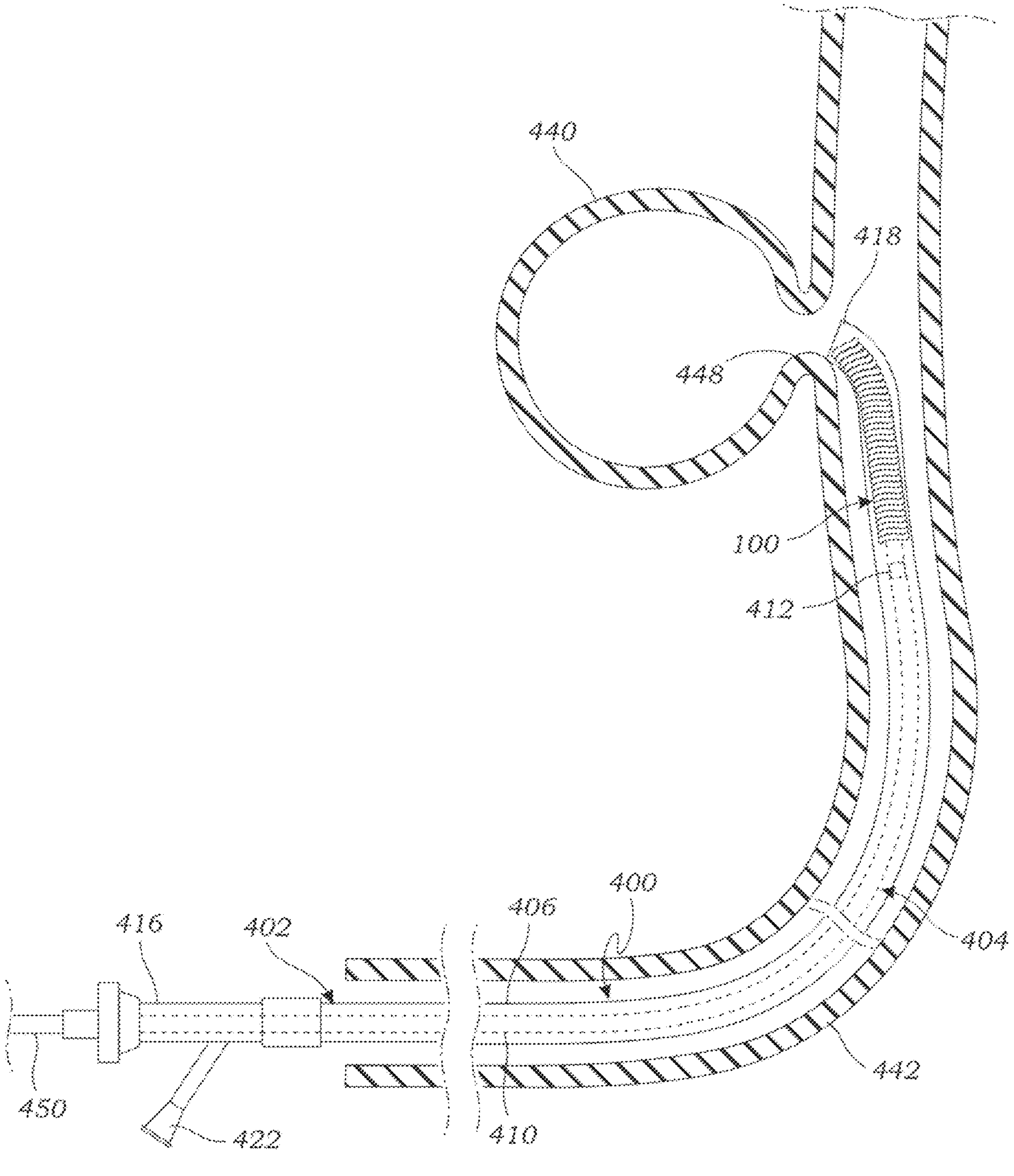
FIG. 17 is a cross-sectional, side view depicting the vaso-occlusive system of FIGS. 14A and 14B being advanced within the delivery catheter of FIG. 16 for deploying the vaso-occlusive device into the aneurysm.
Figure 18:
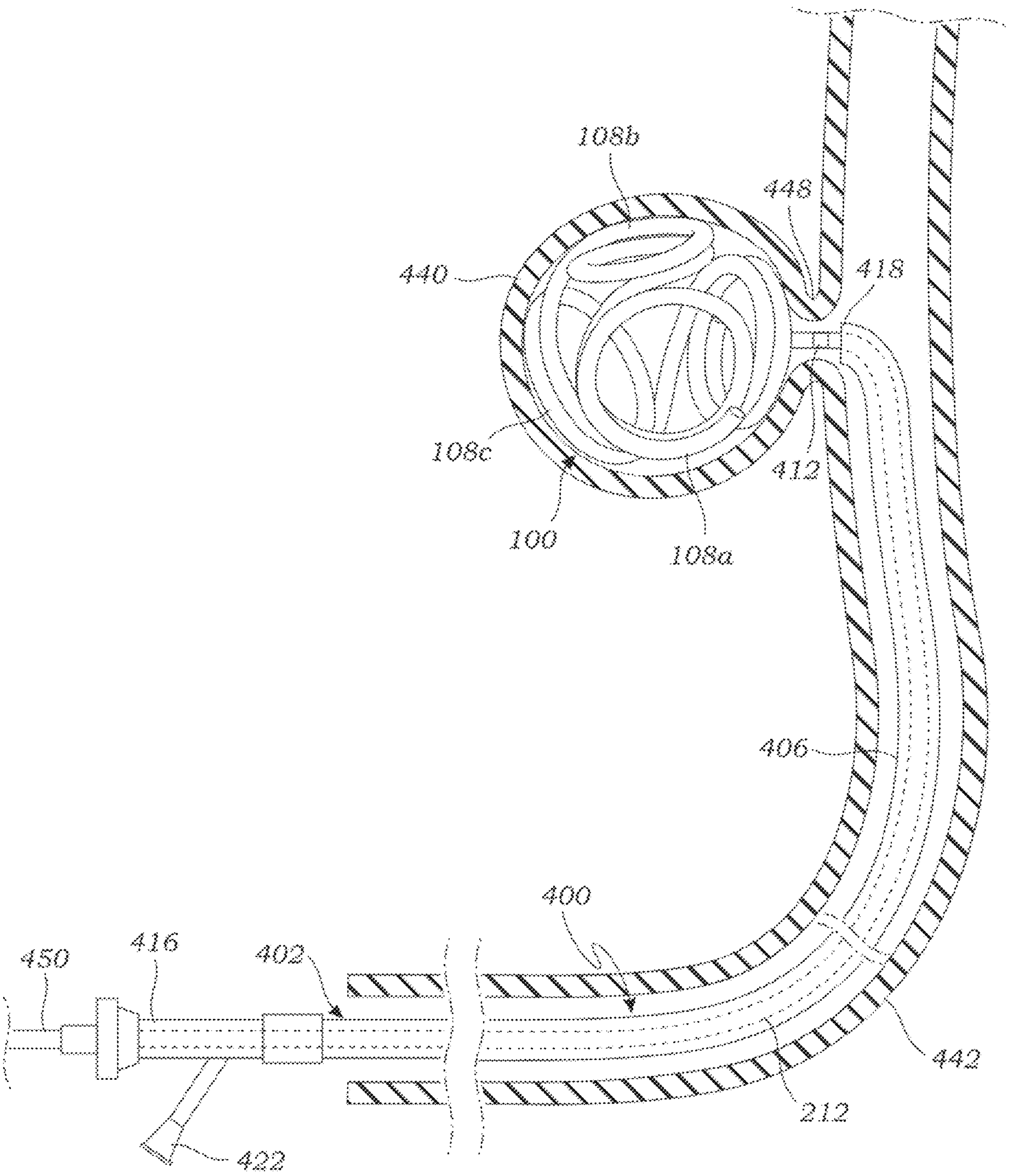
FIG. 18 is a cross-sectional, side view depicting the vaso-occlusive system of FIGS. 14A and 14B with the vaso-occlusive device deployed out of the delivery catheter shown in FIG. 16 and into the aneurysm.
Figure 19:
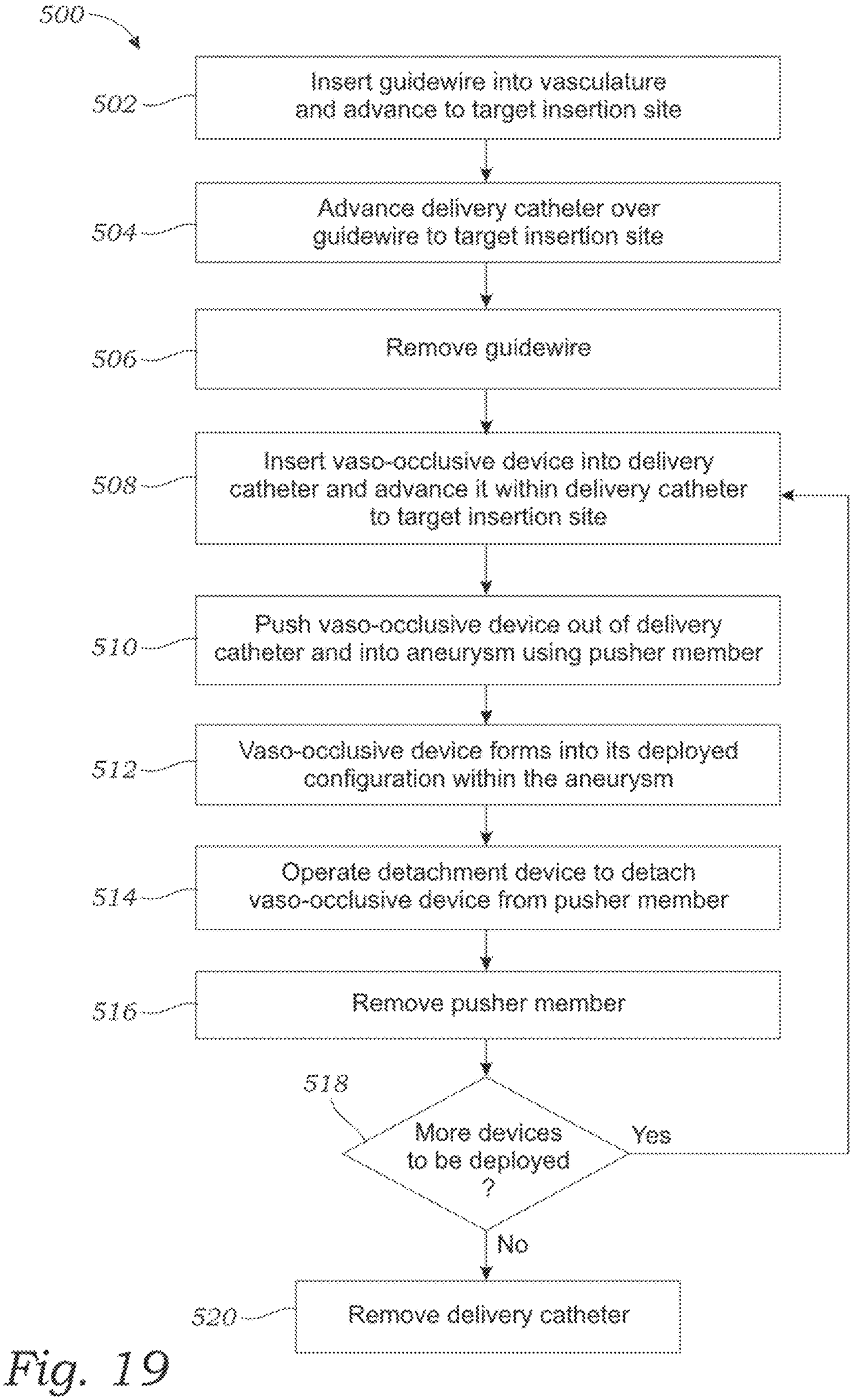
FIG. 19 is a flow chart of an exemplary method of using the vaso-occlusive system of FIGS. 14A and 14B to deploy the vaso-occlusive devices disclosed herein into an aneurysm.

At step 504, the delivery catheter 406 of the delivery assembly 402 is advanced over the guidewire 408 until it is positioned with the open distal end 418 adjacent or within the aneurysmal neck 448 of the aneurysm 440, as shown in FIG. 17. At step 506, the guidewire 408 is pulled out of the delivery catheter 406 leaving the delivery catheter 406 in position. At step 508, the vaso-occlusive assembly 404 is inserted into the delivery catheter 406 of the delivery assembly 402 and advanced within the delivery catheter 406 to position the distal end of the vaso-occlusive device 100 adjacent the distal portion 418 of the delivery catheter 406, as shown in FIG. 18. At this position, the proximal portion 450 of the pusher member 410 remains proximal and outside of the proximal portion 416 of the delivery catheter 406. Prior to inserting the vaso-occlusive device 100 into the delivery catheter 406, the vaso-occlusive device 100 may be pre-installed in a sheath such that the vaso-occlusive device 100 is in its constrained, delivery configuration (primary configuration). The vaso-occlusive device 100 is then inserted into the delivery catheter 406 by placing a distal end of the sheath in abutment with the proximal end 416 of the delivery catheter 406 and extruding the vaso-occlusive device 406 from the sheath into the delivery catheter 406 such that the vaso-occlusive device 100 remains in its delivery configuration within the delivery catheter 206.

At step 510, the vaso-occlusive device 100 is pushed through the lumen 420 of the delivery catheter 406 and distally out of the delivery catheter 406 by pushing on the proximal portion 450 of the pusher member 412. At step 512, as the vaso-occlusive device 100 is pushed out of the open distal end 418 of the delivery catheter 406, the pyramidal portion 104 is advanced through the aneurysmal neck 448 and into the aneurysmal sac 440, the distal portion of the vaso-occlusive device 100 in its delivery configuration (primary configuration) expands into the secondary configuration (deployed configuration), and the distal coils 108 of the pyramidal portion 104 are formed within the aneurysmal sac 240. Also at step 512, as the vaso-occlusive device 100 continues to be advanced out of the delivery catheter 406 via the pusher member 412, the proximal portion of the vaso-occlusive device 100 in its delivery configuration (primary configuration) expands into its secondary configuration (deployed configuration) forming the base portion 106 within aneurysmal sac 440. Once the entire vaso-occlusive device 100 is inserted into the aneurysmal sac 440, at step 514, the detachment device 412 is actuated, activated or otherwise operated to detach the vaso-occlusive device 100 from the pusher-member 410. At step 516, the pusher member 410 is removed from the patient's vasculature 442 by withdrawing it out through the delivery catheter 406. If the single vaso-occlusive device 100 is sufficient to fill and occlude the aneurysm sac 440, then the method 500 proceeds to step 520 in which the delivery catheter 406 is removed from the patient's vasculature 442. If multiple vaso-occlusive devices 100 are being implanted, then the process of steps 508-516 are repeated to deliver a sufficient number of vaso-occlusive devices 100 to fill and occlude the aneurysmal sac 440. After the sufficient number of vaso-occlusive devices 100 are implanted in the aneurysmal sac 440, the delivery catheter 406 is removed at step 520.

Although particular embodiments of the disclosed inventions have been shown and described herein, it will be understood by those skilled in the art that they are not intended to limit the present inventions, and it will be obvious to those skilled in the art that various changes and modifications may be made (e.g., the dimensions of various parts) without departing from the scope of the disclosed inventions, which is to be defined only by the following claims and their equivalents. The specification and drawings are, accordingly, to be regarded in an illustrative rather than restrictive sense. The various embodiments of the disclosed inventions shown and described herein are intended to cover alternatives, modifications, and equivalents of the disclosed inventions, which may be included within the scope of the appended claims.

What is claimed is:

1. A vaso-occlusive device, comprising:

a single wire having a primary configuration in a constrained condition;

wherein the single wire forms a secondary configuration in a relaxed, unconstrained condition, the secondary configuration comprising:

a pyramidal portion comprising a plurality of distal coils wound from the single wire, each distal coil comprising a winding forming a closed loop of greater than 360° wherein the winding has a perimeter which tapers outwardly from an interior of the pyramidal portion at an angle between 5 to 15 degrees, and a transition segment of the wire between each distal coil and connecting each distal coil to an adjacent distal coil, the plurality of distal coils arranged in a tetrahedral pyramidal shape such that each coil lies in a different lateral face of the pyramidal shape, each of the distal coils consisting of from 1⅔ turns to 2 turns having zero pitch between each turn, and the distal coils overlapping in a transition from one distal coil to an adjacent distal coil; and a body portion proximal of the pyramidal portion, the body portion comprising a coil formed from the wire and extending proximally from the pyramidal portion.

2. The vaso-occlusive device of claim 1, wherein the pyramidal shape is a tetrahedral forming a triangular pyramid shape having 3 lateral faces.

3. The vaso-occlusive device of claim 1, wherein the pyramidal shape is a polyhedral shape formed of a polygonal base having n number of sides and n number of lateral faces connecting to an apex.

4. The vaso-occlusive device of claim 1, wherein the primary configuration comprises an elongate helical coil.

5. The vaso-occlusive device of claim 4, wherein the wire is formed from a shape memory material, and the secondary configuration is set by winding the wire on a mandrel and heat treating the wire wound on the mandrel.

6. The vaso-occlusive device of claim 5, wherein the vaso-occlusive device is configured to treat an aneurysm having a diameter to be treated, and each of the distal coils has an average outer diameter between 10 to 90 percent of the diameter of the aneurysm the vaso-occlusive device is configured to treat.

7. The vaso-occlusive device of claim 5, wherein the vaso-occlusive device is configured to treat an aneurysm having a diameter to be treated, and each of the distal coils has an average outer diameter between 55 to 85 percent of the diameter of the aneurysm the vaso-occlusive device is configured to treat.

* * * * *